US012620323B2

(12) United States Patent
Neumann

(10) Patent No.: US 12,620,323 B2
(45) Date of Patent: May 5, 2026

(54) METHODS AND SYSTEMS FOR SELF-FULFILLMENT OF A DIETARY REQUEST

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 830 days.

(21) Appl. No.: 17/517,772

(22) Filed: Nov. 3, 2021

(65) Prior Publication Data

US 2022/0058981 A1 Feb. 24, 2022

Related U.S. Application Data

(63) Continuation-in-part of application No. 16/430,401, filed on Jun. 3, 2019, now Pat. No. 11,200,814.

(51) Int. Cl.
G06F 16/00 (2019.01)
G06F 16/903 (2019.01)
(Continued)

(52) U.S. Cl.
CPC ... G09B 19/0092 (2013.01); G06F 16/90335 (2019.01); G16H 20/60 (2018.01); G16H 50/20 (2018.01)

(58) Field of Classification Search
None
See application file for complete search history.

(56) References Cited

U.S. PATENT DOCUMENTS 5,598,505 A * 1/1997 Austin .................... G10L 15/20
704/226
6,819,782 B1 * 11/2004 Imagawa .................. G06T 7/74
382/218
(Continued)

FOREIGN PATENT DOCUMENTS

CN 105022908 4/2014
JP 2006221533 2/2005
KR 20140129559 4/2013

OTHER PUBLICATIONS

Petot GJ et al.; Sep. 1998; An artificial intelligence system for computer-assisted menu planning.;https://www.ncbi.nlm.nih.gov/pubmed/9739801.

(Continued)

*Primary Examiner* — Polina G Peach
(74) *Attorney, Agent, or Firm* — Caldwell LLC

(57) ABSTRACT

A system for self-fulfillment includes at least a server. The at least a server is designed and configured to receive training data, wherein receiving the training data further comprises receiving at least a dietary request and at least a correlated alimentary process label. The at least a server is configured to receive at least a dietary request from a user device. The at least a server generates at least an alimentary instruction set as a function of the at least a dietary request from the user device and the training data. The at least a server generates at least a self-fulfillment instruction set as a function of the at least an alimentary instruction set containing at least a self-fulfillment action. The at least a server receives at least a user entry containing an alimentary self-fulfillment action.

18 Claims, 16 Drawing Sheets

(51) Int. Cl.
    *G09B 19/00*         (2006.01)
    *G16H 20/60*        (2018.01)
    *G16H 50/20*        (2018.01)

(56) References Cited

U.S. PATENT DOCUMENTS

| | | | |
|---|---|---|---|
| 6,980,999 B1 | 12/2005 | Grana | |
| 8,060,383 B2 | 11/2011 | Badinelli | |
| 9,483,957 B1 * | 11/2016 | Fuemmeler | G09B 5/125 |
| 9,552,461 B2 | 1/2017 | Harrison | |
| 10,207,859 B2 | 2/2019 | Minvielle | |
| 10,573,000 B2 * | 2/2020 | Chen | G06F 18/2148 |
| 2001/0025279 A1 | 9/2001 | Krulak et al. | |
| 2003/0059747 A1 | 3/2003 | Yoshida et al. | |
| 2004/0002838 A1 * | 1/2004 | Oliver | G06V 30/274 |
| | | | 703/2 |
| 2010/0003647 A1 | 1/2010 | Brown et al. | |
| 2010/0198605 A1 | 8/2010 | Saulet | |
| 2011/0301433 A1 * | 12/2011 | Sadowsky | G16H 20/70 |
| | | | 600/300 |
| 2011/0318717 A1 | 12/2011 | Adamowicz | |
| 2014/0156295 A1 | 6/2014 | Cooper | |
| 2014/0220516 A1 | 8/2014 | Siani | |
| 2014/0236950 A1 * | 8/2014 | Kim | G06V 10/95 |
| | | | 707/737 |
| 2014/0255882 A1 | 9/2014 | Hadad et al. | |
| 2015/0012291 A1 * | 1/2015 | Stut | G16Z 99/00 |
| | | | 705/2 |
| 2015/0142464 A1 * | 5/2015 | Rusin | G16H 40/67 |
| | | | 705/2 |
| 2015/0185974 A1 | 7/2015 | Holman et al. | |
| 2016/0071432 A1 * | 3/2016 | Kurowski | G16H 20/30 |
| | | | 434/236 |
| 2016/0078571 A1 | 3/2016 | Singh | |
| 2016/0085923 A1 | 3/2016 | Lacombe | |
| 2016/0196404 A1 * | 7/2016 | Liu | G16H 20/30 |
| | | | 705/2 |
| 2016/0364528 A1 * | 12/2016 | Reicher | G16H 10/20 |
| 2018/0001184 A1 * | 1/2018 | Tran | G16H 50/20 |
| 2018/0113987 A1 * | 4/2018 | Zhu | G16H 40/63 |
| 2018/0137941 A1 * | 5/2018 | Chen | G06N 3/08 |
| 2018/0174687 A1 * | 6/2018 | Ayvazian | G16H 50/70 |
| 2018/0240359 A1 * | 8/2018 | Hujsak | G06N 5/022 |
| 2018/0293638 A1 * | 10/2018 | Simpson | G16B 40/00 |
| 2019/0062813 A1 * | 2/2019 | Amin | B01L 3/5635 |
| 2020/0257697 A1 * | 8/2020 | Bhabesh | G06F 16/1824 |
| 2020/0294234 A1 * | 9/2020 | Rance | G06F 18/22 |
| 2021/0374132 A1 * | 12/2021 | Yang | G06F 16/2457 |

OTHER PUBLICATIONS

Khan AS: Feb. 2003; Building a case-based diet recommendation system without a knowledge engineer.; https://www.ncbi.nlm.nih.gov/pubmed/12636977.

* cited by examiner

METHODS AND SYSTEMS FOR SELF-FULFILLMENT OF A DIETARY REQUEST

CROSS-REFERENCE TO RELATED APPLICATIONS

This application is a continuation-in-part of Non-provisional application Ser. No. 16/430,401 filed on Jun. 3, 2019 and entitled "METHODS AND SYSTEMS FOR SELF-FULFILLMENT OF A DIETARY REQUEST," the entirety of which is incorporated herein by reference.

FIELD OF THE INVENTION

The present invention generally relates to the field of artificial intelligence. In particular, the present invention is directed to methods and systems for self-fulfillment of a dietary request.

BACKGROUND

Effective and accurate analysis of data to produce practical and useful instruction sets is challenging. Generating accurate instruction sets is complex in part due to the vast amount of data to be analyzed. Current solutions fail to account for the intricate complexities involved in both producing and receiving meaningful instruction sets.

SUMMARY OF THE DISCLOSURE

These and other aspects and features of non-limiting embodiments of the present invention will become apparent to those skilled in the art upon review of the following description of specific non-limiting embodiments of the invention in conjunction with the accompanying drawings.

In an aspect, a system for self-fulfillment of a dietary request includes at least a server, wherein the at least a server is designed and configured to receive an alimentary instruction set as a function of a user dietary request generate at least a self-fulfillment instruction set, the self-fulfillment instruction set including a data structure identifying a plurality of self-fulfilling actions a user can take to self-fulfill a suggested nourishment requirement, as a function of at least a self-fulfillment action, wherein generating the at least a self-fulfillment instruction set includes receiving training data including a plurality of data entries, each data entry of the plurality of data entries including at least an alimentary instruction and at least a correlated self-fulfillment action datum, training a machine-learning model as a function of the training data, and generating the at least a self-fulfillment instruction set as a function of the alimentary instruction set and the machine-learning model, receive at least a user entry containing an alimentary self-fulfillment action, and generate a modified self-fulfillment instruction set as a function of the alimentary self-fulfillment action.

In another aspect, a method of self-fulfillment of a dietary request includes receiving, by at least a server, an alimentary instruction set as a function of a user dietary request, generating, by the at least a server, at least a self-fulfillment instruction set, the self-fulfillment instruction set including a data structure identifying a plurality of self-fulfilling actions a user can take to self-fulfill a suggested nourishment requirement, as a function of at least a self-fulfillment action, wherein generating the at least a self-fulfillment instruction set includes receiving training data including a plurality of data entries, each data entry of the plurality of data entries including at least an alimentary instruction and at least a correlated self-fulfillment action datum, training a machine-learning model as a function of the training data, generating the at least a self-fulfillment instruction set as a function of the alimentary instruction set and the machine-learning model, receiving, by the at least a server, at least a user entry containing an alimentary self-fulfillment action, and generating, by the at least a server a modified self-fulfillment instruction set as a function of the alimentary self-fulfillment action.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Aspects of the present disclosure are directed towards methods and systems for self-fulfillment of a dietary request.

In an embodiment, at least a server may receive at least a request for a dietary request. In an embodiment, a user may generate at least a request for a dietary request. The at least a request for a dietary request may be generated by a user as a function of user preference for a certain diet, or as a function of a user report of a previous diagnosis of a medical condition such as Celiac Disease or gout, or as part of an elimination diet. In an embodiment, at least a server may generate at least an alimentary instruction set as a function of the at least a dietary request and training data. The at least a server may generate at least a self-fulfillment instruction set which may contain different ways in which a user may self-fulfill an alimentary instruction set. The at least a server may then receive at least a user entry describing how a user self-fulfilled. User entry may then be matched against alimentary instruction set and/or self-fulfillment instruction set to generate more accurate and customizable entries over time.

Figure 1:
FIG. 1 is a block diagram illustrating an exemplary embodiment of a system for self-fulfillment of a dietary request.

Turning now to FIG. 1, a system 100 for self-fulfillment of a dietary request is illustrated. System 100 includes at least a server 102. At least a server 102 may include any computing device as described herein, including without limitation a microcontroller, microprocessor, digital signal processor (DSP) and/or system on a chip (SoC) as described herein. At least a server 102 may be housed with, may be incorporated in, or may incorporate one or more sensors of at least a sensor. Computing device may include, be included in, and/or communicate with a mobile device such as a mobile telephone or smartphone. At least a server 102 may include a single computing device operating independently, or may include two or more computing device operating in concert, in parallel, sequentially or the like; two or more computing devices may be included together in a single computing device or in two or more computing devices. At least a server 102 with one or more additional devices as described below in further detail via a network interface device. Network interface device may be utilized for connecting a at least a server 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 102 may include but is not limited to, for example, a at least a server 102 or cluster of computing devices in a first location and a second computing device or cluster of computing devices in a second location. At least a server 102 may include one or more computing devices dedicated to data storage, security, distribution of traffic for load balancing, and the like. At least a server 102 may distribute one or more computing tasks as described below across a plurality of computing devices of computing device, which may operate in parallel, in series, redundantly, or in any other manner used for distribution of tasks or memory between computing devices. At least a server 102 may be implemented using a "shared nothing"

architecture in which data is cached at the worker, in an embodiment, this may enable scalability of system 100 and/or computing device.

With continued reference to FIG. 1, at least a server 102 and/or one or more modules operating thereon may be designed and/or configured to perform any method, method step, or sequence of method steps in any embodiment described in this disclosure, in any order and with any degree of repetition. For instance, at least a server 102 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 102 and/or one or more modules operating thereon may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, server 102 is configured to receive a training set 104 including a plurality of data entries, each data entry of the plurality of data entries including at least an element of first dietary request data 106 and at least a correlated alimentary process label 108 and receive at least a dietary request from a user device. At least a dietary request as used in this disclosure includes a request for a particular diet, food, ingredient, food group, nutrition plan, supplement, style of eating, lifestyle, and/or nutrition. At least a dietary request may include a request for a particular type of diet such as Atkins, Paleo, Whole 30, gluten free, ketogenic, dairy free, Mediterranean, soy free, and the like. At least a dietary request may include elimination of certain foods or food groups because of a dislike for such foods, an allergy to a food, and/or a sensitivity. For example, at least a dietary request may include a request for an egg free diet based on a user's aversion to eggs. In yet another non-limiting example, at least a dietary request may include a request for a diet free of bell peppers because of a user's previous IgG food sensitivity testing. At least a dietary request may include a request for a diet free of shellfish because of a user's IgE allergic response to shellfish that was diagnosed when a user was a little child. At least a dietary request may include a request for a diet based on religious or moral beliefs such as kosher diet or vegetarian diet. At least a dietary request may include a request to eliminate certain food groups such as a nightshade free diet or a grain free diet. At least a dietary request may include a request to eliminate certain ingredients that may be commonly found in food such as a request for a diet free of monosodium glutamate (MSG) or corn starch. At least a dietary request may include a request for a certain level or quality of ingredients such as locally sourced ingredients, free range meats, wild caught fish, organic produce and the like. At least a dietary request may include a request for a certain diet because of a previously diagnosed medical condition, such as a user who has been previously diagnosed with Candida and is following a low sugar diet. At least a dietary request may include a dietary request based on a certain style of eating that a user prefers, such as low carb, high protein, low fat, and the like. At least a dietary request may include a dietary request as a function of a medication, supplementation, and/or medical treatment or therapy that a user may be undergoing. For example, a user currently taking a medication such as metronidazole may generate at least a dietary request for an alcoholic free diet, while a user currently supplementing with zinc may generate at least a dietary request free of oysters.

Continuing to refer to FIG. 1, server 102 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, server 102 may be configured to receive a training set 104 including a plurality of data entries, each data entry of the training set 104 including at least a first dietary request data 106 and at least a correlated alimentary process label. An "alimentary process label," as used in this disclosure, is an element of data identifying a solution and/or suggestion as to nourishment requirements and/or options contained within a dietary request. Alimentary process label may include nourishment requirements and/or options including potential foods, meals, ingredients, and/or supplements that may be compatible for a user to consume as a function of user's dietary request. For example, a dietary request for a gluten free diet may contain an alimentary process label that contains nourishment options such as gluten free toast, gluten free grains such as buckwheat, rice, and amaranth. In yet another non-limiting example, a dietary request for a raw foods diet may contain an alimentary process label that contains nourishment options including fruits such as strawberries, kiwis, and bananas. At least a first dietary request data 106 may include any data describing the user, user needs, user dietary preferences, and/or user preferences. First dietary request data 106 may include a constitutional restriction such as an injury, a previous diagnosis from a medical professional such as a functional medicine doctor, an allergy or food sensitivity issue, a contraindication to a medication or supplement and the like. For example, a user diagnosed with colitis and currently taking an antibiotic medication such as metronidazole may report a constitutional restriction that includes restrictions on alcohol consumption. At a least a first dietary request data 106 may include religious preferences such as forbidden foods, medical interventions, exercise routines and the like. At least a first dietary request data 106 may include a user's dislike such as for example a user aversion to certain foods or nutrient groups, such as for example an aversion to liver or onions. At least a first dietary request data 106 may include for example a user's likes such as a user's preference to consume animal protein or plant protein. At least a first dietary request data 106 may include for example, a preferred dietary style of eating such as vegetarian, vegan, pescatarian, flexitarian, and the like. At least a first dietary request data 106 may include a preferred style of eating such as for example, paleo, ketogenic, gluten free, grain free, low FODMAP, raw food diet, fruitarian, lacto vegetarianism, ovo vegetarianism, intermittent fasting, Mediterranean diet, carb-conscious, gluten free, nightshade free, dairy free, and the like.

With continued reference to FIG. 1, in each first data element of training set 104, at least an alimentary process label is correlated with at least a first dietary request data 106. In an embodiment, an element of first dietary request data 106 is correlated with at least an alimentary process label where the element of dietary data is located in the same data element and/or portion of data element as the alimentary label; for example, and without limitation, an element of dietary data is correlated with an alimentary label where both element of dietary data and alimentary element are contained within the same first data element of the training set 104. As a further example, an element of dietary data is correlated with an alimentary element where both share a category label as described in further detail below, where each is within a certain distance of the other within an ordered collection of data in data element, or the like. Still further, an element of dietary data may be correlated with an alimentary label where the element of dietary data and the alimentary label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between dietary data and alimentary labels that may exist in training set 104 and/or first data element consistently with this disclosure.

In an embodiment, and still referring to FIG. 1, server 102 may be designed and configured to associate at least an element of a dietary request with a category from a list of significant categories of first dietary request data 106. Significant categories of first dietary request data 106 may include labels and/or descriptors describing types of first dietary request data 106 that are identified as being of high relevance in identifying alimentary process labels 106. As a non-limiting example, one or more categories may identify significant categories of first dietary request data 106 based on degree of relevance to one or more impactful conditions and/or serious adverse events associated with dietary request data. For instance, and without limitation, a particular set of first dietary request data 106 that includes anaphylaxis to shellfish may be recognized as utmost importance for a user to avoid all shellfish containing foods even those foods that may contain hidden ingredients containing shellfish derivatives such as oyster sauce as compared to first dietary request data 106 that includes a dislike of Brussel sprouts, whereby ingestion of Brussel sprouts may not produce an anaphylactic reaction but rather is more indicative of a dislike. As a non-limiting example, and without limitation, first dietary request data 106 describing gluten avoidance such as a gluten intolerance, Celiac Disease, wheat allergy, atopic dermatitis, fructose malabsorption, non-Celiac gluten sensitivity, dermatitis herpetiformis, IgE mediated gluten allergy, IgG mediated gluten sensitivity may be recognized as useful for identifying avoidance of various gluten containing foods and ingredients such as wheat, barley, oats, malt, croutons, corn flakes, couscous, pancakes, beer, brewer's yeast, and flour tortillas. In a further non-limiting example, first dietary request data 106 describing gluten avoidance may be useful for identifying certain categories of foods such as grains, alcoholic beverages, sauces, dressings, baked goods, starches, and the like. Persons skilled in the art, upon reviewing the entirety of this disclosure, will be aware of various additional categories of physiological data that may be used consistently with this disclosure.

Still referring to FIG. 1, server 102 may receive the list of significant categories according to any suitable process; for instance, and without limitation, server 102 may receive the list of significant categories from at least an expert. In an embodiment, server 102 and/or a user device connected to server 102 may provide a graphical user interface 110, which may include without limitation a form or other graphical element having data entry fields, wherein one or more experts, including without limitation clinical and/or scientific experts, may enter information describing one or more categories of dietary data that the experts consider to be significant or useful for detection of conditions; fields in graphical user interface may provide options describing previously identified categories, which may include a comprehensive or near-comprehensive list of types of dietary data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to alimentary labels, where experts may enter data describing alimentary labels and/or categories of alimentary labels the experts consider related to entered categories of dietary request data; for instance, such fields may include drop-down lists or other pre-populated data entry fields listing currently recorded alimentary labels, and which may be comprehensive, permitting each expert to select an alimentary label and/or a plurality of alimentary labels the expert believes to be predicted and/or associated with each category of dietary request data selected by the expert. Fields for entry of alimentary labels and/or categories of alimentary labels may include free-form data entry fields such as text entry fields; as described above, examiners may enter data not presented in pre-populated data fields in the free-form data entry fields. Alternatively or additionally, fields for entry of alimentary labels may enable an expert to select and/or enter information describing or linked to a category of alimentary label that the expert considers significant, where significance may indicate likely impact on longevity, mortality, quality of life, or the like as described in further detail below. Graphical user interface 110 may provide an expert with a field in which to indicate a reference to a document describing significant categories of dietary data, relationships of such categories to alimentary labels, and/or significant categories of alimentary labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of dietary request data, relationships of such categories to alimentary labels, and/or significant categories of alimentary labels may alternatively or additionally be extracted from one or more documents using a language processing module 112. Language processing module 112 may include any hardware and/or software module. Language processing module 112 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 112 may compare extracted words to categories of dietary request data, one or more alimentary process labels, and/or one or more categories of alimentary process labels recorded at server 102; such data for comparison may be entered on server 102 as described above using expert data inputs or the like. In an embodiment, one or more categories may be enumerated, to find total count of mentions in such documents. Alternatively or additionally, language processing module 112 may operate to produce a language processing model. Language processing model may include a program automatically generated by server 102 and/or language processing module 112 to produce associations between one or more words extracted from at least a document and detect associations, including without limitation mathematical associations, between such words, and/or associations of extracted words with categories of dietary data, relationships of such categories to alimentary labels, and/or categories of alimentary labels. Associations between language elements, where language elements include for purposes herein extracted words, categories of dietary data, relationships of such categories to alimentary labels, and/or categories of alimentary labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of dietary request data, a given relationship of such categories to alimentary process labels, and/or a given category of alimentary process labels. As a further example, statistical correlations and/or mathematical associations may include probabilistic formulas or relationships indicating a positive and/or negative association between at least an extracted word and/or a given category of dietary request, a given relationship of such categories to alimentary process labels, and/or a given category of alimentary process labels; positive or negative indication may include an indication that a given document is or is not indicating a category of dietary request data, relationship of such category to alimentary process label, and/or category of alimentary labels is or is not significant. For instance, and without limitation, a negative indication may be determined from a phrase such as "whole wheat bread was not found to be compatible with a gluten free diet," whereas a positive indication may be determined from a phrase such as "coconut milk was found to be compatible with a lactose free diet" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at server 102, or the like.

Still referring to FIG. 1, language processing module 112 and/or server 102 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of dietary data, a given relationship of such categories to alimentary labels, and/or a given category of alimentary labels. There may be a finite number of category of dietary data, a given relationship of such categories to alimentary labels, and/or a given category of alimentary labels to which an extracted word may pertain; an HMM inference algorithm, such as the forward-backward algorithm or the Viterbi algorithm, may be used to estimate the most likely discrete state given a word or sequence of words. Language processing module 112 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 112 may use a corpus of documents to generate associations between language elements in a language processing module 112, and server 102 may then use such associations to analyze words extracted from one or more documents and determine that the one or more documents indicate significance of a category of dietary data, a given relationship of such categories to labels, and/or a given category of alimentary labels. In an embodiment, server 102 may perform this analysis using a selected set of significant documents, such as documents identified by one or more experts as representing good science, good clinical analysis, or the like; experts may identify or enter such documents via graphical user interface as described below in reference to FIG. 4, or may communicate identities of significant documents according to any other suitable method of electronic communication, or by providing such identity to other persons who may enter such identifications into server 102. Documents may be entered into server 102 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, server 102 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of dietary data, a given relationship of such categories to alimentary labels, and/or a given category of alimentary labels is entered via graphical user interface, alternative submission means, and/or extracted from a document or body of documents as described above, an entry or entries may be aggregated to indicate an overall degree of significance. For instance, each category of dietary data, relationship of such categories to alimentary labels, and/or category of alimentary labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of dietary data, relationships of such categories to alimentary labels, and/or categories of alimentary labels may be ranked according significance scores, for instance by ranking categories of dietary data, relationships of such categories to alimentary labels, and/or categories of alimentary labels higher according to higher significance scores and lower according to lower significance scores. Categories of dietary data, relationships of such categories to alimentary labels, and/or categories of alimentary labels may be eliminated from current use if they fail a threshold comparison, which may include a comparison of significance score to a threshold number, a requirement that significance score belong to a given portion of ranking such as a threshold percentile, quartile, or number of top-ranked scores.

Still referring to FIG. 1, server 102 may detect further significant categories of dietary data, relationships of such categories to alimentary labels, and/or categories of alimentary labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, server 102 may be configured, for instance as part of receiving the training set 104, to associate at least correlated first alimentary label 110 with at least a category from a list of significant categories of alimentary labels. Significant categories of alimentary labels may be acquired, determined, and/or ranked as described above. As a non-limiting example, alimentary labels may be organized according to relevance to and/or association with a list of significant foods or food groups. A list of significant foods or food groups may include, without limitation, foods having generally acknowledged impact on dietary request. For example, a dietary request such as a grain free diet may be associated with a list of significant foods such as actual grains, grain containing condiments such as ketchup that contains starch thickening agents, grain containing breakfast foods such as pastries and cereals, grain containing frozen foods, grain containing meats and the like.

With continued reference to FIG. 1, server 102 may be configured to receive at least a dietary request from a user device. At least a dietary request may include any of the dietary requests as described above. User device may include any of the user devices as described in more detail below. In an embodiment, at least a dietary request may be received from a computing device. Computing device includes any of the computing devices as described herein. In an embodiment, server 102 may receive at least a dietary request from a computing device such as when server 102 may receive at least a dietary request from a nutrition plan and computing device may generate one or more dietary requests that may match requested nutrition values as established in nutritional plan.

With continued reference to FIG. 1, server 102 may include an alimentary instruction label learner 114, the alimentary instruction label learner 114 designed and configured to generate a correlated alimentary process label. Alimentary instruction label learner 114 may include any hardware and/or software module. Alimentary instruction label learner 114 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, alimentary instruction label learner 114 may be designed and configured to generate at least an alimentary instruction set by creating at least a first machine-learning model 116 relating first dietary request data 106 to alimentary labels using the training set 104 and generating the at least an alimentary instruction set using the first machine-learning model 116; at least a first machine-learning model 116 may include one or more models that determine a mathematical relationship between first dietary request data 106 and alimentary labels. An "alimentary instruction set" as used in this disclosure is a data structure containing a solution and/or suggestion as to nourishment requirements and/or preferences contained within at least a dietary request. Alimentary instruction set may include meals, foods, food groups, ingredients, supplements and the like that may be compatible with at least a dietary request. For example, alimentary instruction set may include a list of three possible meals that may be compatible with at least a dietary request for a dairy free diet. In yet another non-limiting example, alimentary instruction set may include food groups compatible with at least a dietary request such as a dietary request for a paleo diet may include recommendations as to food groups that are compatible including meats, fish, poultry, fats, vegetables, and fruits. Machine-learning models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, machine-learning algorithms may generate alimentary instruction sets as a function of a classification of at least an alimentary label. Classification as used herein includes pairing or grouping alimentary labels as a function of a shared commonality. Classification may include for example, groupings, pairings, and/or trends between dietary data and current alimentary label, future alimentary label, and the like. In an embodiment, machine-learning algorithms may examine relationships between a future propensity of a user to require a new alimentary instruction set based on current dietary data. Machine-learning algorithms may include any and all algorithms as performed by any modules, described herein for alimentary instruction label learner 114. For example, machine-learning algorithms may relate a dietary request such as a grain free diet to a user's future propensity to require an alimentary instruction set containing a recommendation to consume high fiber foods. Machine-learning algorithms may examine precursor dietary requests and future propensity to report a subsequent dietary request. For example, machine-learning algorithms may examine a user dietary request for a gluten free diet with a future propensity to report a subsequent dairy free diet. In yet another non-limiting example, machine learning algorithms may examine varying degrees of dietary requests and restrictions. For example, machine-learning algorithms may examine a user dietary request for Atkins diet with a future propensity to report a less restrictive dietary request such as the South Beach Diet. In yet another non-limiting example, machine-learning algorithms may examine a user dietary request for a gluten free diet with a future propensity to report a more restrictive dietary request such as a ketogenic diet. Machine-learning algorithms may examine a user dietary request for vegetarian diet with a future propensity to report a request for a vegan diet. Machine-learning algorithms may examine degree of dietary restriction requests and development of food allergies over time. For example, machine-learning algorithms may examine a user dietary request for an elimination diet with a future propensity to report a less restrictive diet as foods are reintroduced. Machine-learning algorithms may examine dietary requests by categories, such as demographics including geographic location, age, sex, marital status, profession, income, and the like. For example, machine learning algorithms may examine user dietary requests in California versus user dietary requests in Maine. Machine-learning algorithms may examine dietary requests including several categories such as user dietary requests in men between the ages of 45-55 in Alaska versus user dietary requests among females age 18-24 in Alabama. Machine-learning algorithms may examine trends among dietary requests generated such as for example, a dietary request by a user for vegetarian options and subsequent requests by the user for carnivore dietary requests.

Continuing to refer to FIG. 1, machine-learning algorithm used to generate first machine-learning model 116 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms May include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, alimentary instruction label learner 114 may generate alimentary instruction set using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training set 104; the trained network may then be used to apply detected relationships between elements of first dietary request data 106 and alimentary labels.

With continued reference to FIG. 1, machine-learning algorithms may include unsupervised processes; unsupervised processes may, as a non-limiting example, be executed by an unsupervised learning module executing on server 102 and/or on another computing device in communication with server 102, which may include any hardware or software module as described as described herein. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, alimentary instruction label learner 114 and/or server 102 may perform an unsupervised machine learning process on training set 104, which may cluster data of training set 104 according to detected relationships between elements of the training set 104, including without limitation correlations of elements of first dietary request data 106 to each other and correlations of alimentary labels to each other; such relations may then be combined with supervised machine learning results to add new criteria for alimentary instruction label learner 114 to apply in relating first dietary request data 106 to alimentary labels. As a non-limiting, illustrative example, an unsupervised process may determine that a first element of dietary data closely with a second element of dietary data, where the first element has been linked via supervised learning processes to a given alimentary label, but the second has not; for instance, the second element may not have been defined as an input for the supervised learning process, or may pertain to a domain outside of a domain limitation for the supervised learning process. Continuing the example a close correlation between first element of first dietary request data 106 and second element of first dietary request data 106 may indicate that the second element is also a good predictor for the alimentary label; second element may be included in a new supervised process to derive a relationship or may be used as a synonym or proxy for the first dietary data by alimentary label learner 114.

Still referring to FIG. 1, server 102 and/or alimentary instruction label learner 114 may detect further significant categories of dietary data, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, alimentary instruction label learner 114 and/or server 102 may continuously or iteratively perform unsupervised machine-learning processes to detect relationships between different elements of the added and/or overall data. Use of unsupervised learning may greatly enhance the accuracy and detail with which system may detect alimentary labels.

With continued reference to FIG. 1, unsupervised processes may be subjected to domain limitations. For instance, and without limitation, an unsupervised process may be performed regarding a comprehensive set of data regarding one person, such as demographic information including age, sex, race, geographical location, profession, and the like. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of dietary data, a group of people having a shared value for an element and/or category of alimentary label, and/or a group of people having a shared value and/or category of alimentary label; as illustrative examples, cohort could include all people requesting a gluten free diet, all people requesting a dairy free diet, all people requesting a grain free diet, all people requesting a vegetarian diet or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1, alimentary instruction label learner 114 may alternatively or additionally be designed and configured to generate an alimentary instruction set by executing a lazy learning process as a function of the training set 104 and the at least a dietary request; lazy learning processes may be performed by a lazy learning module executing on server 102 and/or on another computing device in communication with server 102, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an alimentary label associated with a dietary request, using training set 104. As a non-limiting example, an initial heuristic may include a ranking of alimentary labels according to relation to a test type of at least a dietary request, one or more categories of dietary data identified in test type of at least a dietary request, and/or one or more values detected in at least a dietary request; ranking may include, without limitation, ranking according to significance scores of associations between elements dietary data and alimentary labels, for instance as calculated as described above. Heuristic may include selecting some number of highest-ranking associations and/or alimentary labels. Alimentary instruction label learner 114 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate alimentary outputs as described in this disclosure, including without limitation lazy learning applications of machine-learning algorithms as described in further detail below.

Continuing to refer to FIG. 1, alimentary instruction label learner 114 may generate a plurality of alimentary labels having different implications for a particular person. For instance, where the at least a dietary request includes a request for a gluten free diet, alimentary instruction sets may be consistent with recommendations for meals containing grains such as rice, quinoa, teff, millet, buckwheat, amaranth, sorghum and the like. In such a situation, alimentary instruction label learner 114 and/or server 102 may perform additional processes to resolve ambiguity. Processes may include presenting multiple possible results to a user, informing the user that one or more dietary preferences are needed to determine a more definite alimentary label, such as a user preference for a gluten free grain of quinoa over millet. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, alimentary instruction label learner 114 and/or server 102 may operate a further algorithm to determine which of the multiple outputs is most likely to be correct; algorithm may include use of an additional supervised and/or unsupervised model. Alternatively or additionally, alimentary instruction label learner 114 may perform one or more lazy learning processes using a more comprehensive set of user data to identify a more probably correct result of the multiple results. Results may be presented and/or retained with rankings, for instance to advise a user of the relative probabilities of various alimentary labels being correct; alternatively or additionally, alimentary labels associated with a probability of correctness below a given threshold and/or alimentary labels contradicting results of the additional process, may be eliminated. As a non-limiting example, a dietary request for a vegetarian diet may lead to animal containing meat products such as beef, chicken, and lamb from being eliminated from a list of alimentary labels for a user while alimentary labels containing animal derived dairy products such as yogurt, cheese, and milk may be retained. Similarly, a dietary request for a vegan diet may eliminate all animal derived products but retain all plant sourced products including tofu, soybeans, beans, seitan, tempeh, lentils, and the like. Persons skilled in the art, upon reviewing the entirety of this disclosure, will be aware of various ways in which additional processing may be used to determine relative likelihoods of alimentary labels on a list of multiple alimentary labels, and/or to eliminate some labels from such a list. Alimentary instruction set may be provided to user output device as described in further detail below.

With continued reference to FIG. 1, system 100 includes an alimentary instruction set generator module operating on the at least a server. The alimentary instruction set generator module may include any hardware and/or software module as described in this disclosure. Alimentary instruction set generator module is designed and configured to generate at least an alimentary instruction set as a function of the at least a dietary request and the training data. In an embodiment, alimentary instruction set 120 is a data structure containing a solution and/or suggestion to nourishment requirements as requested in the at least a dietary request. Alimentary instruction set may contain suggestions as to foods and/or meals that a user may consume that may meet requirements and/or specifications of at least a dietary request. the at least a dietary request and training data. For example, at least a dietary request containing a request for a dairy free diet may be utilized to generate an alimentary instruction set that includes a suggestion for breakfast that includes oatmeal topped with coconut milk. In yet another non-limiting example, at least a dietary request for a vegetarian diet may be utilized to generate an alimentary instruction set that includes a meal containing tofu, spinach, and rice. In an embodiment, alimentary instruction set generator module may be configured to modify alimentary instruction set as a function of the at least a user entry as described in more detail below.

With continued reference to FIG. 1, alimentary instruction set 120 may be generated upon receiving at least an element of user data including a constitutional restriction. Element of user data as used herein, is any element of data describing the user, user needs, and/or user preferences. At least an element of user data may include a constitutional restriction. At least a constitutional restriction may include any constitutional reason that a user may be unable to engage in an alimentary instruction set process; at least a constitutional restriction may include a contraindication such as an injury, a diagnosis such as by an informed advisor including a functional medicine doctor, an allergy or food sensitivity issue, a contraindication due to a medication or supplement that a user may be taking. For example, a user diagnosed with a hypercholesteremia and currently taking a cholesterol lowering medication such as a statin may report a constitutional restriction that includes an inability to consume grapefruit containing foods and food products.

With continued reference to FIG. 1, alimentary instruction set may be generated upon receiving at least an element of user data including at least a user preference. At least a user preference may include, without limitation, any preference to engage in or eschew any alimentary instruction set process. At least a user preference may include for example religious preferences such as forbidden foods, medical interventions, exercise routines and the like. For example, a user who is of Catholic faith may report a religious preference to not consume animal products on Fridays during lent. At least a user preference may include a user's dislike such as for example a user aversion to certain foods or nutrient groups, such as for example an aversion to eggs or an aversion to beets. At least a user preference may include for example a user's likes such as a user's preference to consume animal products or full fat dairy and the like. In an embodiment, alimentary instruction set 120 may be transmitted by alimentary instruction set module 118 to a user such as to a user client device 134, utilizing any of the transmission methodologies as described herein any network transmissions.

With continued reference to FIG. 1, server 102 includes a self-fulfillment instruction set generator module 122. Self-fulfillment instruction set generator module 122 may include any hardware and/or software module. Self-fulfillment instruction set generator module 122 is designed and configured to generate at least a self-fulfillment instruction set as a function of the at least an alimentary instruction set containing at least a self-fulfillment action. Self-fulfillment instruction set 124 as used herein, is a data structure containing suggestions to be provided to the user to explain different ways in which a user can self-fulfill alimentary instruction set 120. Self-fulfilled as used herein, includes any action or step a user may perform or partake in based on alimentary instruction set. For example, self-fulfillment may include shopping for ingredients, ordering a takeout meal, creating a grocery list for items to purchase at a grocery store, ordering a meal kit, cooking a meal at home, purchasing a pre-packaged meal at a grocery store, purchasing ingredients at a farmer's market, consuming a meal at a restaurant, ordering a meal from a meal preparatory kitchen, and the like. Self-fulfillment instruction set generator module 122 may be configured to transmit a self-fulfillment instruction set to a user such as to user client device 134. Transmission may occur utilizing any of the transmission methodologies as described herein including any network transmissions. Self-fulfillment instruction set 124 may be generated as a function of user geolocation. User location including geographic location of a user may be utilized to generate a self-fulfillment instruction set that may contain ingredients or selections that may be available to a user in a certain geographical location. For example, a user with an alimentary instruction set that contains a recommendation to consume fish products may receive a self-fulfillment instruction set 124 that contains suggestions as to consume salmon, herring, and cod. In an embodiment, self-fulfillment instruction set may be generated as a function of geolocation of a user. For example, a user with a dietary request for a pescatarian diet who is located in Seattle, Washington may receive a self-fulfillment instruction set 124 to increase consumption of locally available wild fish such as yellow perch, walleye, and striped bass, while a user with a dietary request for a pescatarian diet who is located in Naples, Florida may receive a self-fulfillment instruction set to increase one's consumption of locally available wild fish such as red snapper, black grouper, and Florida pompano. In an embodiment, self-fulfillment instruction set 124 may include a plurality of different suggestions as to ways in which user can self-fulfill alimentary instruction set 120. For example, self-fulfillment instruction set may include suggested recipes a user may wish to cook, suggested groceries a user may wish to purchase, suggested meals a user may wish to consume, suggested meal plans a user may wish to follow, suggested eating habits a user may wish to follow, suggested restaurants a user may wish to eat at and the like. In an embodiment, self-fulfillment instruction set may include suggestions based on user location. For example, user may receive a suggested grocery list based on grocery stores in user's area where user is physically present.

With continued reference to FIG. 1, self-fulfillment instruction set generator module 122 may include self-fulfillment learner 126. Self-fulfillment learner 126 may contain any hardware or software module suitable for use as alimentary instruction label learner 114 as described above. Self-fulfillment learner 126 may include a machine-learning module as described above, self-fulfillment learner may perform any machine-learning process or combination of processes suitable for use by alimentary instruction label learner 114 as described above. For instance and without limitation, self-fulfillment learner 126 may be configured to create a second machine-learning model 128 relating self-fulfillment instruction sets to alimentary process labels and/or user entries containing an alimentary self-fulfillment action. Second machine-learning model 128 may be generated according to any process, process steps, or combination of processes and/or process steps suitable for creation of first machine-learning model. In an embodiment, self-fulfillment learner 126 may use data from training set 104; for instance, self-fulfillment learner 126 may use lazy learning and/or model generation to determine relationships between elements of dietary data, in combination with or instead of alimentary labels, which may include, without limitation, a subset of self-fulfillment labels corresponding to self-fulfillment actions. For example, user entry, as described in more detail below, may contain a description pertaining to how user self-fulfilled an alimentary instruction set, such as by shopping for groceries at a local grocery store. Subsequent self-fulfillment instruction sets 146 may be generated based on trends and data collected from user entries. User entries that contain trends and/or repeat habits established by a user may be utilized in machine-learning algorithms to generate subsequent self-fulfillment instruction sets 146. For example, a user entry that contains self-fulfillment actions that include actions such as cooking meals at home may be utilized to generate subsequent self-fulfillment instruction sets that focuses on new recipes as opposed to potential restaurants a user may want to visit. In yet another example, a user entry that contains self-fulfillment actions such as ordering takeout from a restaurant may be utilized to generate subsequent self-fulfillment instruction sets that may not focus on new recipes or grocery shopping lists but instead may focus on different restaurants a user may want to try.

With continued reference to FIG. 1, self-fulfillment learner 126 may perform machine-learning algorithms using a loss function analysis utilizing linear regression based on past interactions between a user and system 100 and self-fulfillment instruction sets to generate self-fulfillment instruction sets. In an embodiment, self-fulfillment learner 126 may compare one or more self-fulfillment options to a mathematical expression representing an optimal combination of self-fulfillment variables. Mathematical expression may include a linear combination of variables, weighted by coefficients representing relative importance of each variables in generating an optimal self-fulfillment action. For instance, a variable such as total transit time in seconds of a self-fulfillment action may be multiplied by a first coefficient representing the importance of total transit time, a total cost of a self-fulfillment action may be multiplied by a second coefficient representing the importance of cost, a degree of variance from an self-fulfillment instruction set may be represented as another parameter, which may be multiplied by another coefficient representing the importance of that variable, a degree of variance from a requested recipe may be multiplied by an additional coefficient representing an importance of that variable, and/or a variable representing a degree of variance from one or more dietary restrictions may be provided a coefficient representing the importance of such a variance; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, self-fulfillment learner may calculate variables of each of a plurality of self-fulfillment actions, calculate an output of mathematical expression using the variables, and select a self-fulfillment action that produces an output having the lowest size, according to a given definition of "size," of the set of outputs representing each of the plurality of self-fulfillment actions; size may, for instance, included absolute value, numerical size, or the like. Selection of different loss functions may result in identification of different self-fulfillment actions as generating minimal outputs;

for instance, where transit time is associated in a first loss function with a large coefficient or weight, a self-fulfillment action having a short transit time may minimize the first loss function, whereas a second loss function wherein transit time has a smaller coefficient but degree of variance from a dietary restriction has a larger coefficient may produce a minimal output for a different self-fulfillment action having a longer transit time but more closely hewing to a dietary restriction.

Alternatively or additionally, and still referring to FIG. 1, each self-fulfillment action may be represented by a mathematical expression having the same form as mathematical expression; self-fulfillment learner 126 may compare the former to the latter using an error function representing average difference between the two mathematical expressions. Error function may, as a non-limiting example, be calculated using the average difference between coefficients corresponding to each variable. A self-fulfillment action having a mathematical expression minimizing the error function may be selected, as representing an optimal expression of relative importance of variables to a system or user. In an embodiment, error function and loss function calculations may be combined; for instance, a self-fulfillment action resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to self-fulfillment action variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options.

With continued reference to FIG. 1, self-fulfillment learner 126 may perform machine-learning algorithms using a loss function analysis utilizing linear regression based on past interactions between a user and system 100 and self-fulfillment instruction sets. Self-fulfillment learner may generate a loss function of user specific variables and minimize the loss function. Self-fulfillment learner 126 may generate self-fulfillment instruction set 124 utilizing loss function analysis. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Self-fulfillment learner 126 may utilize variables to model relationships between past interactions between a user and system 100 and self-fulfillment instruction sets. In an embodiment loss function analysis may utilize variables that may impact user interactions and/or self-fulfillment instruction sets. Variables may include user's habits, such as if user shops for groceries, how often user prepares meals at home, how often user eats out at restaurants or fast food stops, and the like. Variables may include for example, ingredient standard which may include scores for a user's desire to consume organic or locally sourced ingredients. For example, a user may desire local ingredients that are sourced from within a certain distance, such as local ingredients from within 25 miles of user' primary residence. A user may desire a certain percentage of ingredients to be locally sourced, such as for example 85% of ingredients may be locally sourced. Variables may include for example ingredient requirements which may include scores for how different products and/or ingredients may fulfill a user's alimentary instruction set needs, such as for example products that may contain gluten for a user with a dietary request for a gluten free diet or products that contain monosodium glutamate (MSG) for a user with a dietary request for a diet free of MSG. Variables may include cost such as for example how much money a user is willing to pay for an ingredient or quality and how cost may factor into a user's overall budget for food. For example, a user with a fixed budget may be satisfied eating a nonorganic apple and avoiding the apple core where the pesticides reside as compared to spending more money on an organic apple. Variables may include travel time based on geographical location such as for example how far a user is willing to travel to a grocery store or restaurant to acquire ingredients or a meal. Variables may include a user preference for certain foods or food groups such as a user who doesn't wish to consume foods containing monosodium glutamate (MSG) or a user who seeks to avoid trans fats. Variables may include user preferences such as a user's preference to consume user's favorite foods or meals. Variables may include availability of certain products and ingredients such as for example, availability of fresh seafood in Denver, Colorado or availability of fresh avocados in wintertime in Boston, Massachusetts. Loss function analysis may be user specific so as to create algorithms and outputs that are customize to variables for an individual user. User behaviors and user past responses may be utilized as training data to generate outputs. Variables contained within loss function analysis may be weighted and given different numerical scores. Variables may be stored and utilized to predict subsequent outputs. Outputs may seek to predict user behavior and past user interactions with system 100 and self-fulfillment instruction sets.

With continued reference to FIG. 1, system 100 includes fulfillment module 130. Fulfillment module 130 may include any suitable hardware or hardware module. Fulfillment module 130 is designed and configured to receive a user entry containing an alimentary self-fulfillment action. In an embodiment, fulfillment module 130 may receive a user entry containing an alimentary self-fulfillment action from a user client device 134 operated by a user. User client device may include any of the user client devices as described in more detail below. Alimentary self-fulfillment action as used herein, includes any user entry containing any information as to how a user self-fulfilled. User entry may include a user generated response that may include text, graphics, photographs, descriptions, sentences, words, selections, choices, and the like describing how a user self-fulfilled an alimentary instruction set 120. For example, user entry may contain a photograph of a meal a user consumed for breakfast the previous day. For example, alimentary instruction set 120 may contain a recommendation for a user to consume foods such as fresh fruits, vegetables, animal protein products, and non-dairy milk such as coconut milk and/or almond milk and to avoid grains for a user with a dietary request for a paleo diet. User entry may include a user generated response that may contain a description of a meal user consumed for lunch consisting of a chopped salad topped with avocado, walnuts, and chicken. User entry may include a graphic such as a photograph a user may take of user's meal and transmit to fulfillment module. In an embodiment, user may select from a list certain foods user may have consumed. In an embodiment, user may generate a user entry at timed intervals, such as after every meal user consumes or at the end of each day. In an embodiment, user may generate a user entry sporadically or at untimed intervals. For example, a user who has an alimentary instruction set 120 that includes recommendations that may be restrictive such as following a nightshade free diet may not generate a user entry when user is traveling on vacation and is unable to follow nightshade free diet. Fulfillment module 130 may be configured to match user entry containing an alimentary instruction set as a function of the user entry to at least a self-fulfillment instruction set as described in more detail below. Fulfillment module 130 may be configured to match user entry containing an alimentary instruction set as a function off the user entry to at least an alimentary instruction set as described in more detail below.

With continued reference to FIG. 1, system 100 may include a client-interface module 132. Client-interface module 132 may include any suitable hardware or software module. Client-interface module 132 may designed and configured to transmit alimentary instruction set to at least a user client device 134 associated with the user. A user client device 134 may include, without limitation, a display in communication with server 102; display may include any display as described herein. A user client device 134 may include an addition computing device, such as a mobile device, laptop, desktop computer, or the like. Output may be displayed on at least a user client device 134 using an output graphical user interface.

Figure 2:
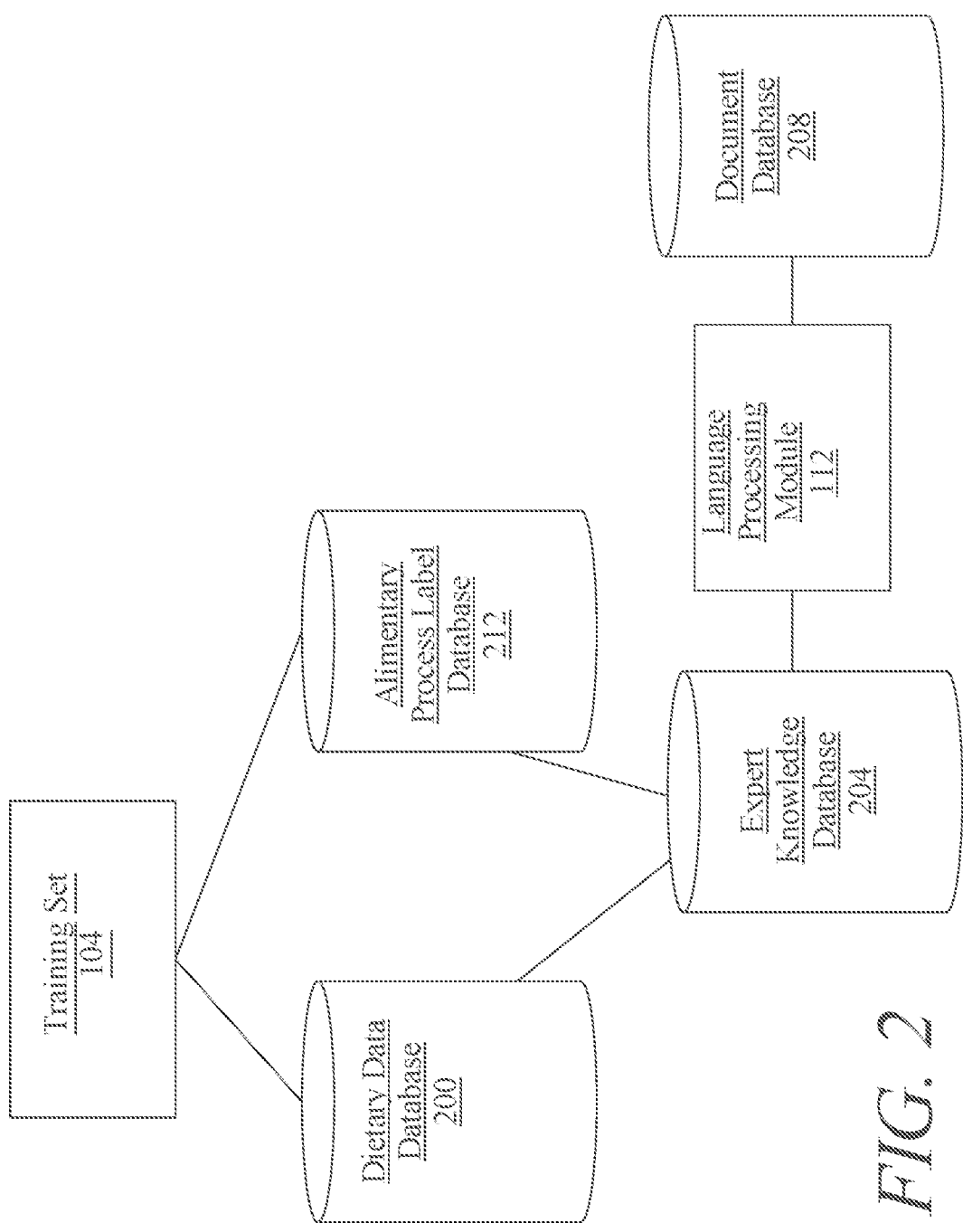
FIG. 2 is a block diagram illustrating embodiments of data storage facilities for use in disclosed systems and methods.

Referring now to FIG. 2, data incorporated in training set 104 and/or may be incorporated in one or more databases. As a non-limiting example, one or elements of dietary data may be stored in and/or retrieved from dietary data database 200. A dietary data database 200 may include any data structure for ordered storage and retrieval of data, which may be implemented as a hardware or software module. A dietary data database 200 may be implemented, without limitation, as a relational database, a key-value retrieval datastore such as a NOSQL database, or any other format or structure for use as a datastore that a person skilled in the art would recognize as suitable upon review of the entirety of this disclosure. A dietary data database 200 may include a plurality of data entries and/or records corresponding to elements of dietary data as described above. Data entries and/or records may describe, without limitation, data concerning particular dietary requests that have been collected; entries may describe particular foods and/or ingredients that are compatible with one or more dietary requests, which may be listed with related alimentary labels. For example, a dietary request for a gluten free diet and an unrelated dietary request for a Mediterranean diet may both may both be compatible with ingredients that include wild fish, grains such as buckwheat, polenta, and millet, and fresh vegetables such as kale, spinach, and tomatoes. Data entries may include alimentary labels and/or other descriptive entries describing results of evaluation of past dietary requests, including alimentary labels that were associated with conclusions regarding likelihood of future dietary requests associated with an initial dietary request. Such conclusions may have been generated by system 100 in previous iterations of methods, with or without validation of correctness by medical professionals such as functional medicine doctors, functional dieticians, functional nutritionists, and the like. Data entries in a dietary data database 200 may be flagged with or linked to one or more additional elements of information, which may be reflected in data entry cells and/or in linked tables such as tables related by one or more indices in a relational database; one or more additional elements of information may include data associating a dietary request with one or more cohorts, including demographic groupings such as ethnicity, sex, age, income, geographical region, or the like. Additional elements of information may include one or more categories of dietary data as described above. Additional elements of information may include descriptions of particular methods used to obtain dietary data, such as without limitation collecting dietary data from experts utilizing expert reports, papers, and/or opinions from experts who practice in a particular field related to a particular dietary request. Persons skilled in the art, upon reviewing the entirety of this disclosure, will be aware of various ways in which data entries in a dietary data database 200 may reflect categories, cohorts, and/or populations of data consistently with this disclosure.

With continued reference to FIG. 2, server 102 may be configured to have a feedback mechanism. In an embodiment, server 102 may be configured to receive a training set 104 generated by system 100. For example, data about a user that has been previously been analyzed by server 102 may be utilized in algorithms by first model 116 and/or second model 128. Such algorithms may be continuously updated as a function of such data. In yet another embodiment, data analyzed by language processing module 112 may be utilized as part of training data generating algorithms by first model 116 and/or second model 128 and/or any other machine learning process performed by server 102.

Figure 3:
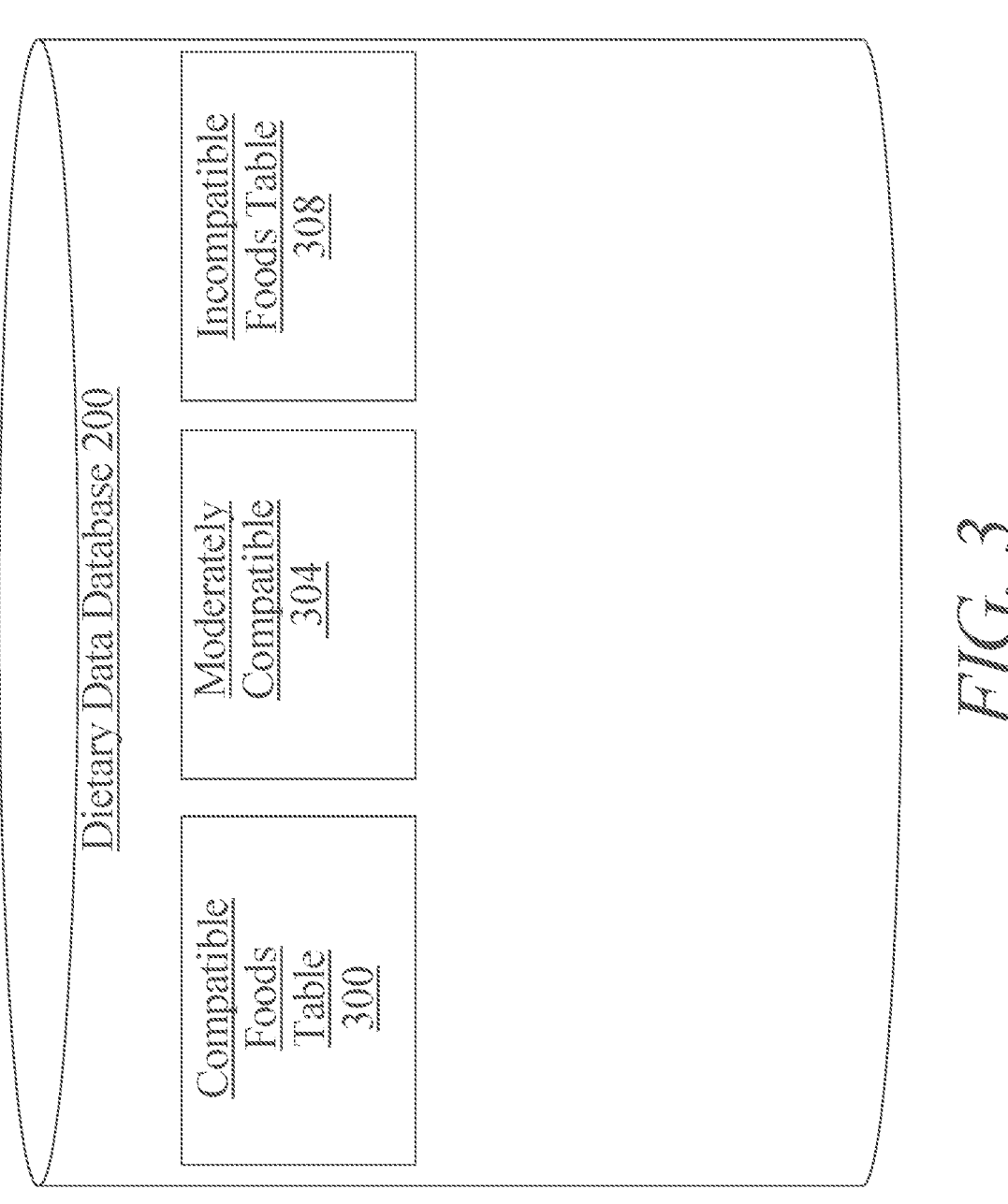
FIG. 3 is a block diagram illustrating an exemplary embodiment of a dietary data database.

Referring now to FIG. 3, one or more database tables in dietary data database 200 may include, as a non-limiting example, a compatible foods table 300. For instance and without limitation, compatible foods table 300 may be a table relating dietary requests to foods that are compatible with a particular dietary request; for instance where a dietary request contains a request for a ketogenic diet foods such as beef tips, ground sirloin and lamb shanks may be compatible with such a request while such foods may not be compatible with a dietary request for a vegan diet. Dietary data database 200 may include moderately compatible food table 304 which may be a table relating dietary request to foods that are moderately compatible with a particular dietary request; for instance where a dietary request contains a request for a gluten free diet from a user with a self-reported gluten intolerance, foods such as certified gluten free oats may be moderately compatible with such a user, while certified gluten free oats may not be compatible for a user following a gluten free diet because of a previous diagnosis of Celiac Disease. For instance and without limitation, dietary data database 200 may include as a non-limiting example, incompatible food table 308. For instance and without limitation, incompatible food table 308 may include a table relating dietary requests to foods that are incompatible with a particular dietary request; for instance where a dietary request contains a request for a corn free diet ingredients such as cornstarch, corn oil, dextrin, maltodextrin, dextrose, fructose, ethanol, maize, and/or sorbitol may be listed. In an embodiment, database tables contained within dietary data database 200 may include groupings of foods by different categories such as grains, meats, vegetables, fruits, sugars and fats, and the like. In an embodiment, database tables contained within dietary data database 200 may include groups of foods by ingredients that a food may be comprised of, for example gravy may contain flour which may contain gluten.

Referring again to FIG. 2, server 102 and/or another device in system 100 may populate one or more fields in dietary data database 200 using expert information, which may be extracted or retrieved from an expert knowledge database 204. An expert knowledge database 204 may include any data structure and/or data store suitable for use as dietary data database 200 as described above. Expert knowledge database 204 may include data entries reflecting one or more expert submissions of data such as may have been submitted according to any process described above in reference to FIG. 1, including without limitation by using first graphical user interface 110 and/or first graphical user interface 110. Expert knowledge database may include one or more fields generated by language processing module 112, such as without limitation fields extracted from one or more documents as described above. For instance, and without limitation, one or more categories of dietary data and/or related alimentary labels and/or categories of alimentary labels associated with an element of physiological state data as described above may be stored in generalized from in an expert knowledge database 204 and linked to, entered in, or associated with entries in a dietary data database 200. Documents may be stored and/or retrieved by server 102 and/or language processing module 112 in and/or from a document database 208; document database 208 may include any data structure and/or data store suitable for use as dietary data database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
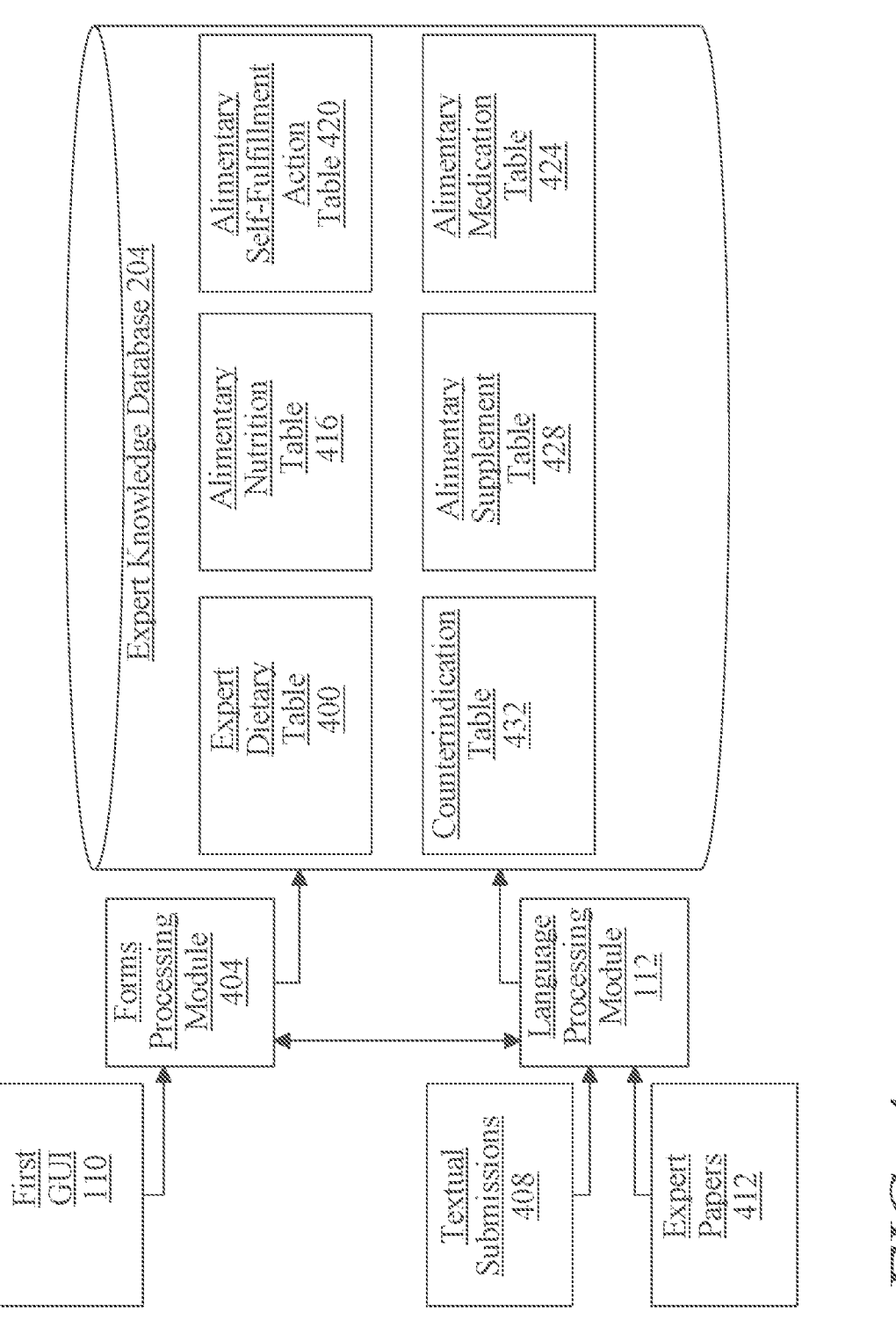
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert dietary table 400. Expert dietary table 400 may be a table relating dietary data as described above to alimentary labels; for instance, where an expert has entered data relating an alimentary label to a category of dietary data and/or to an element of dietary data via first graphical user interface 110 as described above, one or more rows recording such an entry may be inserted in expert dietary table 400. In an embodiment, a forms processing module 404 may sort data entered in a submission via first graphical user interface 110 by, for instance, sorting data from entries in the first graphical user interface 110 to related categories of data; for instance, data entered in an entry relating in the first graphical user interface 110 to an alimentary label may be sorted into variables and/or data structures for storage of alimentary labels, while data entered in an entry relating to a category of dietary data and/or an element thereof may be sorted into variables and/or data structures for the storage of, respectively, categories of dietary data or elements of dietary data. Where data is chosen by an expert from pre-selected entries such as drop-down lists, data may be stored directly; where data is entered in textual form, language processing module 112 may be used to map data to an appropriate existing label, for instance using a vector similarity test or other synonym-sensitive language processing test to map dietary data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 112. Data may be extracted from expert papers 412, which may include without limitation publications in medical and/or scientific journals, by language processing module 112 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert dietary table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more alimentary process labels; expert data populating such tables may be provided, without limitation, using any process described above, including entry of data from first graphical user interface 110 via forms processing module 404 and/or language processing module 112, processing of textual submissions 408, or processing of expert papers 412. For instance, and without limitation, an alimentary nutrition table 416 may list one or more alimentary recommendations based on nutritional instructions, and/or links of such one or more alimentary recommendations to alimentary labels, as provided by experts according to any method of processing and/or entering expert data as described above. As a further example an alimentary self-fulfillment action table 420 may list one or more alimentary processes based on instructions for self-fulfillment actions a user should take, including without limitation self-fulfillment actions such as purchasing groceries at a grocery store, ordering groceries online, ordering a meal at a restaurant, cooking a meal at home, ordering a meal delivery kit, cooking a meal delivery kit, hiring a chef to prepare meals, and/or links of such one or more dietary requests to alimentary labels, as provided by experts according to any method of processing and/or entering expert data as described above. As an additional example, an alimentary supplement table 428 may list one or more alimentary processes based on nutritional supplements, such as vitamin pills or the like, and/or links of such one or more dietary requests to alimentary labels, as provided by experts according to any method of processing and/or entering expert data as described above. Alimentary supplement table 428 may list a recommended supplement a user may consider taking as a function of a dietary request. For example, a dietary request such as a vegan diet may be recommended to supplement with B vitamins. As a further non-limiting example, an alimentary medication table 424 may list one or more alimentary processes based on medications, including without limitation over-the-counter and prescription pharmaceutical drugs, and/or links of such one or more dietary requests to alimentary labels, as provided by experts according to any method of processing and/or entering expert data as described above. Alimentary medication table 424 may recommend a dietary request as a function of a medication a user may be taking. For example, a user taking an antibiotic such as metronidazole may be recommended to eliminate alcohol, while a user taking a medication such as doxycycline may be recommended to eliminate dairy containing products. As an additional example, a counterindication table 432 may list one or more counterindications for one or more dietary requests; counterindications may include, without limitation allergies to one or more foods, medications, and/or supplements, side-effects of one or more medications and/or supplements, interactions between medications, foods, and/or supplements, exercises that should not be used given one or more dietary request.

Referring now to FIG. 2, system 100 may include or communicate with an alimentary process label database 212; an alimentary process label database 212 may include any data structure and/or datastore suitable for use as a dietary data database 200 as described above. An alimentary process label database 212 may include one or more entries listing labels associated with one or more alimentary processes as described above, including any dietary requests correlated with alimentary labels in training set 104 as described above; alimentary process labels may be linked to or refer to entries in alimentary label database 212 to which alimentary process labels correspond. Linking may be performed by reference to historical data concerning alimentary labels, such as ingredients, products, food items, lifestyle, and/or dietary choices associated with dietary requests in the past; alternatively or additionally, a relationship between an alimentary process label and a data entry in alimentary process label database 212 may be determined by reference to a record in an expert knowledge database 204 linking a given alimentary process label to a given category of alimentary label as described above. Entries in alimentary process label database 212 may be associated with one or more categories of alimentary labels as described above, for instance using data stored in and/or extracted from an expert knowledge database 204.

With continued reference to FIG. 2, training set 104 may be populated by retrieval of one or more records from dietary data database 200 and/or alimentary process label database 212; in an embodiment, entries retrieved from dietary data database 200 and/or alimentary process label database 212 may be filtered and or select via query to match one or more additional elements of information as described above, so as to retrieve a training set 104 including data belonging to a given cohort, demographic population, or other set, so as to generate outputs as described below that are tailored to a person or persons with regard to whom system 100 classifies dietary requests to alimentary labels as set forth in further detail below. Persons skilled in the art, upon reviewing the entirety of this disclosure, will be aware of various ways in which records may be retrieved from dietary data database 200 and/or alimentary process label database 212 to generate a training set to reflect individualized group data pertaining to a person of interest in operation of system and/or method, including without limitation a person with regard to whom at least a dietary request is being evaluated. Server may alternatively or additionally receive a training set 104 and store one or more entries in dietary database 200 and/or alimentary process label database 212 as extracted from elements of training set 104.

With continued reference to FIG. 2, training set 104 may be populated by matching user entries with dietary requests. For example, training set 104 may be populated by analyzing user entries such as by language processing module 112 to analyze what types of meals and/or food choices that a user made. User entries as described in more detail below, may be received by fulfillment module and may contain an alimentary self-fulfillment action. User entries may then be matched against an associated dietary request. For example, a user entry that contains a description of a meal a user cooked at home may be analyzed by language processing module 112 to determine if the ingredients contained within the meal complied with the dietary request generated by the user. Such data may then be utilized as training set 104. Training set 104 may also be obtained by performing a loss function and optimizing roots as described in more detail below.

With continued reference to FIG. 2, server 102 may receive an update to one or more elements of data represented in training set 104 and may perform one or more modifications to training set 104, or to dietary data database 200, expert knowledge database 204, and/or alimentary process label database 212 as a result. For instance, a dietary request may turn out to have been erroneously recorded such as when a user requested a dietary request but may have never provided a user entry; server 102 may remove it from training set 104, dietary data database 200, expert knowledge database 204, and/or alimentary process label database 212 as a result. As a further example, a medical and/or academic paper, or a study on which it was based, may be revoked; server 102 may remove it from training set 104, dietary data database 200, expert knowledge database 204, and/or alimentary process label database 212 as a result. Information provided by an expert may likewise be removed if the expert loses credentials or is revealed to have acted fraudulently.

Continuing to refer to FIG. 2, elements of data training set 104, dietary database 200, expert knowledge database 204, and/or alimentary process label database 212 may have temporal attributes, such as timestamps; server 102 may order such elements according to recency, select only elements more recently entered for training set 104 and/or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Figure 5:
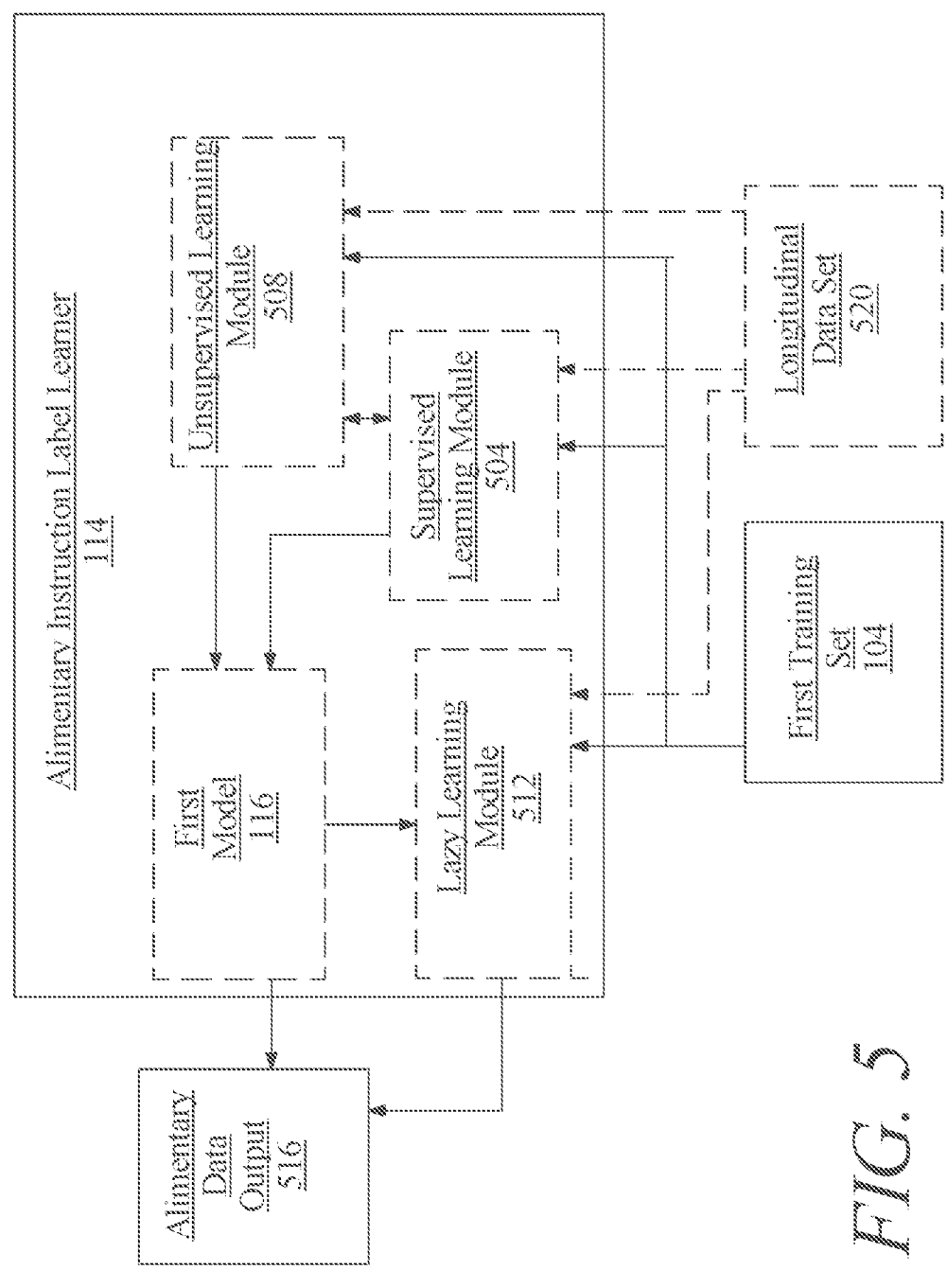
FIG. 5 is a block diagram illustrating an exemplary embodiment of an alimentary process label database.

Referring now to FIG. 5, an exemplary embodiment of alimentary instruction label learner 114 is illustrated. Alimentary instruction label learner 114 may be configured to perform one or more supervised learning processes, supervised learning processes may be performed by a supervised learning module 504 executing on server 102 and/or on another computing device in communication with server 102, which may include any hardware or software module. Machine-learning algorithms used by alimentary instruction label learner 114 may include supervised machine-learning algorithms, which may, as a non-limiting example be executed using a supervised learning module 504 executing on server 102 and/or on another computing device in communication with server, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of dietary data as inputs, alimentary labels as outputs, and a scoring function representing a desired form of relationship to be detected between elements of dietary data and alimentary labels; scoring function may, for instance, seek to maximize the probability that a given element of dietary data and/or combination of elements of dietary data is associated with a given alimentary label and/or combination of alimentary labels to minimize the probability that a given element of dietary data and/or combination of elements of dietary data is not associated with a given alimentary label and/or combination of alimentary labels. Scoring function may be expressed as a risk function representing an "expected loss" of an algorithm relating inputs to outputs, where loss is computed as an error function representing a degree to which a prediction generated by the relation is incorrect when compared to a given input-output pair provided in training set 104. Persons skilled in the art, upon reviewing the entirety of this disclosure, will be aware of various possible variations of supervised machine learning algorithms that may be used to determine relation between elements of dietary data and alimentary labels. In an embodiment, one or more supervised machine-learning algorithms may be restricted to a particular domain for instance, a supervised machine-learning process may be performed with respect to a given set of parameters and/or categories of parameters that have been suspected to be related to a given set of alimentary labels, and/or are specified as linked to a particular field of dietary requests. As a non-limiting example, a particular set of foods and/or food groups may be typically consumed by certain diets such as for example, coconut meat consumed on a ketogenic diets or raw foods diet, and a supervised machine-learning process may be performed to relate those foods and/or food groups to the various dietary requests; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate alimentary labels. Additional supervised learning processes may be performed without domain restrictions to detect, for instance, previously unknown and/or unsuspected relationships between dietary data and alimentary labels.

With continued reference to FIG. 5, alimentary instruction label learner 114 may perform one or more unsupervised machine-learning processes as described above; unsupervised processes may be performed by an unsupervised learning module 508 executing on server 102 and/or on another computing device in communication with server 102, which may include any hardware or software module. For instance, and without limitation, alimentary instruction label learner 114 and/or server 102 may perform an unsupervised machine learning process on training set 104, which may cluster data of training set 104 according to detected relationships between elements of the training set 104, including without limitation correlations of alimentary labels to each other; such relations may then be combined with supervised machine learning results to add new criteria for alimentary instruction label learner 114 to apply in relating dietary data to alimentary labels. As a non-limiting, illustrative example, an unsupervised process may determine that a first dietary request correlates closely with a second dietary request, where the first dietary request has been linked via supervised learning processes to a given alimentary label, but the second has not; for instance, the second dietary request may not have been defined as an input for the supervised learning process, or may pertain to a domain outside of a domain limitation for the supervised learning process. Continuing the example, a close correlation between first dietary request and second dietary request may indicate that the second dietary request is also a good match for the alimentary label; second dietary request may be included in a new supervised process to derive a relationship or may be used as a synonym or proxy for the first dietary request by alimentary instruction label learner 114. Unsupervised processes performed by alimentary instruction label learner 114 may be subjected to any domain limitations suitable for unsupervised processes as described above.

Still referring to FIG. 5, server 102 and/or alimentary instruction label learner 114 may detect further significant categories of dietary requests, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to server 102, alimentary instruction label learner 114 and/or server 102 may continuously or iteratively perform unsupervised machine-learning processes to detect relationships between different elements of the added and/or overall data; in an embodiment, this may enable server 102 to use detected relationships to discover new correlations between known dietary requests, alimentary labels, and one or more elements of data in large bodies of data, such as nutritional, health, lifestyle, and/or dietary-related data, enabling future supervised learning and/or lazy learning processes to identify relationships between, e.g., particular dietary requests and particular alimentary labels. Use of unsupervised learning may greatly enhance the accuracy and detail with which system may detect alimentary labels.

Continuing to view FIG. 5, alimentary instruction label learner 114 may be configured to perform a lazy learning process as a function of the training set 104 and the at least a dietary request to produce the at least an alimentary output; a lazy learning process may include any lazy learning process. Lazy learning processes may be performed by a lazy learning module 512 executing on server 102 and/or on another computing device in communication with server 102, which may include any hardware or software module.

With continued reference to FIG. 5, alimentary instruction label learner 114 may generate a plurality of alimentary labels having different implications for a particular person. For instance, where a dietary request includes a request for a grain free diet, various dietary choices may be generated as alimentary labels associated with the dietary request, such as alimentary labels that may include protein choices such as lamb, veal, beef, chicken, cod, salmon, shrimp, and herring. In such an instance, alimentary instruction label learner 114 and/or server 102 may perform additional processes to resolve ambiguity. Processes may include presenting multiple possible results to a user, informing the user of various options that may be available, and/or that follow-up question may be required to select an appropriate choice such as asking a user what protein choices user prefers, likes, and/or dislikes. Alternatively or additionally, processes may include additional machine learning steps. For instance, alimentary instruction label learner 114 may perform one or more lazy learning processes using a more comprehensive set of user data to identify a more probably correct result of the multiple results. Alimentary instruction label learner 114 may generate alimentary data output 516 as a function of training set 104 and/or first model 116. Results may be presented and/or retained with rankings, for instance to advise a user of the relative probabilities of various alimentary labels being correct or ideal choices for a given user; alternatively or additionally, alimentary labels associated with a probability of success or suitability below a given threshold and/or alimentary labels contradicting results of the additional process, may be eliminated. As a non-limiting example, an additional process may reveal that a user is allergic to salmon, and consumption of salmon may be eliminated as an alimentary label to be presented.

Continuing to refer to FIG. 5, alimentary instruction label learner 114 may be designed and configured to generate further training data and/or to generate outputs using longitudinal data 520. As used herein, longitudinal data 520 may include a temporally ordered series of data concerning the same user, or the same cohort of users; for instance, longitudinal data 520 may describe a series of alimentary instruction sets generated for a user over a period of time such as over the course of a month or year. Longitudinal data 520 may relate to a series of samples tracking response of one or more elements of dietary data recorded regarding a person undergoing one or more alimentary processes linked to one or more alimentary process labels. Alimentary instruction label learner 114 may track one or more elements of dietary data and fit, for instance, a linear, polynomial, and/or splined function to data points; linear, polynomial, or other regression across larger sets of longitudinal data, using, for instance, any regression process as described above, may be used to determine a best-fit graph or function for the effect of a given alimentary process over time on a dietary request. Functions may be compared to each other to rank alimentary processes; for instance, an alimentary process associated with a steeper slope in curve representing improvement in a dietary request, and/or a shallower slope in a curve representing a slower decline, may be ranked higher than an alimentary process associated with a less steep slope for an improvement curve or a steeper slope for a curve marking a decline. Alimentary processes associated with a curve and/or terminal data point representing a value that does not associate with a previously detected alimentary process label may be ranked higher than one that is not so associated. Information obtained by analysis of longitudinal data 520 may be added to alimentary process database and/or training set.

Figure 6:
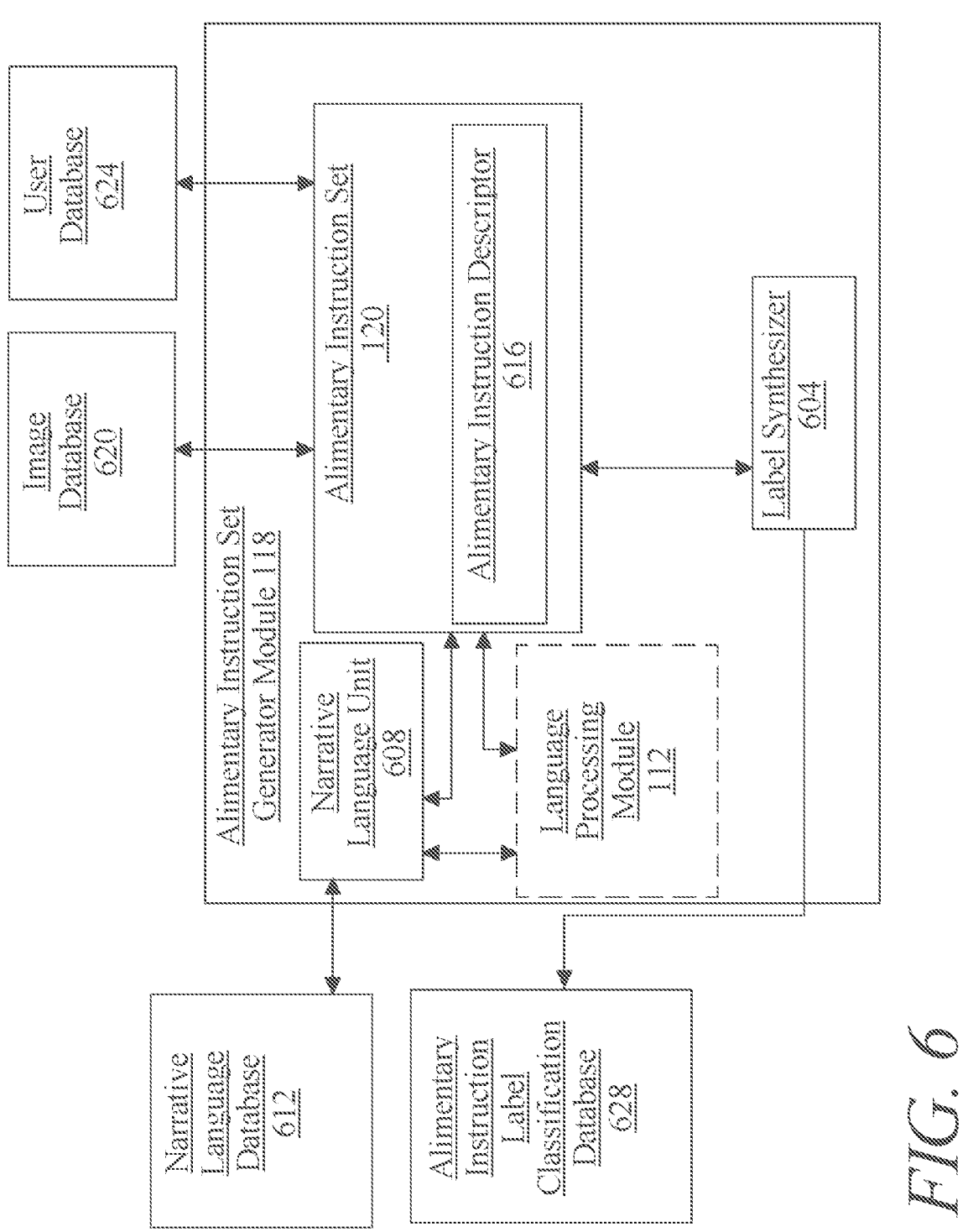
FIG. 6 is a block diagram illustrating an exemplary embodiment of an alimentary instruction set generator module.

Referring now to FIG. 6, an exemplary embodiment of alimentary instruction set module 118 is illustrated. Alimentary instruction set generator module 118 is configured to generate at least an alimentary instruction set as a function of the at least a dietary request from a user and the training set. Alimentary instruction set generator module 118 may produce at least an alimentary instruction set process descriptor 616 using at least an alimentary instruction set output. In an embodiment, alimentary instruction set generator module may include a label synthesizer 604 as described in more detail below.

With continued reference to FIG. 6, the alimentary instruction set may be transmitted to a user via a graphical user interface coupled to user client device 134 associated with user operating in or subscribing to network 100. Alimentary instruction set 120 may be utilized to aid a user in performing alimentary instruction set 120 through self-fulfilling. Self-fulfillment may include any food preparation, consuming food through food delivery, arranging for a vitamin/supplement coaching service, constitutional supplement delivery service, grocery shopping, arranging grocery delivery, picking up take-out from a food preparation center, buying a carry away meal at a grocery store or health food store, preparing a meal kit, cooking a meal from scratch in one's home, having a chef deliver and/or prepare a meal at a user's home or work, and the like.

Continuing to refer to FIG. 6, alimentary instruction set generator module 118 is designed and configured to generate an alimentary instruction set 120 based on dietary request from the user and the training data. In an embodiment, alimentary instruction set generator module 118 may generate alimentary instruction set 120 based on the integration of data associated with training set 104, any applicable external sources, and any applicable database within system 100. Generation of alimentary instruction set 120 may include identification of one or more alimentary instructions as a function of dietary request, and insertion of the one or more alimentary instructions in the alimentary instruction set 120; for instance, alimentary instruction set 120 may be formed, wholly or partially, by aggregating alimentary instructions and combining the aggregated alimentary instructions using narrative language module, narrative language database, image database, or the like.

With continued reference to FIG. 6, alimentary instruction set generator module 118 may include a label synthesizer 604. Label synthesizer 604 may include any suitable software or hardware module. In an embodiment, label synthesizer 604 may be designed and configured to combine a plurality of labels in at least a prognostic output together to provide maximally efficient data presentation. Combination of labels together may include elimination of duplicate information. For instance, label synthesizer 604 and/or at least a server 102 may be designed and configure to determine a first alimentary label of the at least an alimentary label is a duplicate of a second alimentary label of the at least an alimentary label and eliminate the first alimentary label. Determination that a first alimentary label is a duplicate of a second alimentary label may include determining that the first alimentary label is identical to the second alimentary label; for instance, an alimentary label generated from test data presented in one dietary request of at least a dietary request may be the same as an alimentary label generated from test data presented in a second dietary request of at least a dietary request. As a further non-limiting example, a first alimentary label may be synonymous with a second alimentary label, where detection of synonymous labels may be performed, without limitation, by a language processing module 112 as described above.

Continuing to refer to FIG. 6, label synthesizer 604 may group alimentary labels according to one or more classification systems relating the alimentary labels to each other. For instance, alimentary instruction set generator module 118 and/or label synthesizer 604 may be configured to determine that a first alimentary label of the at least an alimentary label and a second alimentary label of the at least an alimentary label belong to a shared category. A shared category may be an ingredient, food and/or or category of food or ingredient to which each of first alimentary label and second alimentary label belongs; as an example, lactose free diet and dairy free diet may be examples of dietary requests which may in turn share of a category of food ingredients such as milk alternatives including coconut milk, almond milk, hemp milk, oat milk, and/or soy milk.

With continued reference to FIG. 6, alimentary data may be identified and aggregated into a subset of applicable alimentary data based on at least a dietary request and training set 104. In an embodiment, alimentary instruction set 120 may comprise a plurality of alimentary data specific to user that is able to be used by machine learning and artificial intelligence systems in order to continuously update or modify training sets, and alimentary instruction set 120 based on updated or progressions associated with implementation of alimentary instruction set 120 by user. Alimentary data and non-alimentary data may include compilations of instruction sets received over a period of time, the compilations may account for improvements or modifications associated with user. Alimentary instruction set 120 may further include instructions over time, in which the alimentary instructions may change in response to changes in a user's data and/or prognosis. Alternatively or additionally, system 100 may periodically iterate through one or more processes as described in this disclosure, such that repeated reevaluations may modify alimentary instruction set 120 as information concerning user and/or dietary requests obtained from the user change over time.

With continued reference to FIG. 6, in one embodiment, alimentary instruction set generator module 118 may be configured to generate alimentary instruction set process descriptor 616 by converting one or more alimentary instruction set labels into narrative language. As a non-limiting example, alimentary instruction set generator module 118 may include and/or communicate with narrative language unit 608, which may be configured to determine an element of narrative language associated with at least an alimentary instruction set label and include the element of narrative language in current alimentary instruction set label descriptor. Narrative language unit 608 may implement this, without limitation, by using a language processing module 112 to detect one or more associations between alimentary instruction set labels, or lists of alimentary instruction set labels, and phrases and/or statements of narrative language. Alternatively or additionally, narrative language unit 608 may retrieve one or more elements of narrative language from narrative language database 612, which may contain one or more tables associating alimentary instruction set labels and/or groups of alimentary instruction set labels with words, sentences, and/or phrases of narrative language. One or more elements of narrative language may be included in alimentary instruction set, for instance for display to a user as text describing a current alimentary instruction set status of the user. Alimentary instruction set process descriptor 616 may further include one or more images; one or more images may be retrieved by alimentary instruction set generator module from an image database 620, which may contain one or more tables associating alimentary instruction set labels, groups of alimentary instruction set labels, alimentary instruction set process descriptors 616, or the like with one or more images.

With continued reference to FIG. 6, in an embodiment, relationships between alimentary labels and categories may be retrieved from an alimentary instruction label classification database 628, for instance by generating a query using one or more alimentary labels of at least an alimentary output, entering the query, and receiving one or more categories matching the query from the alimentary instruction label classification database 628.

Figure 7:
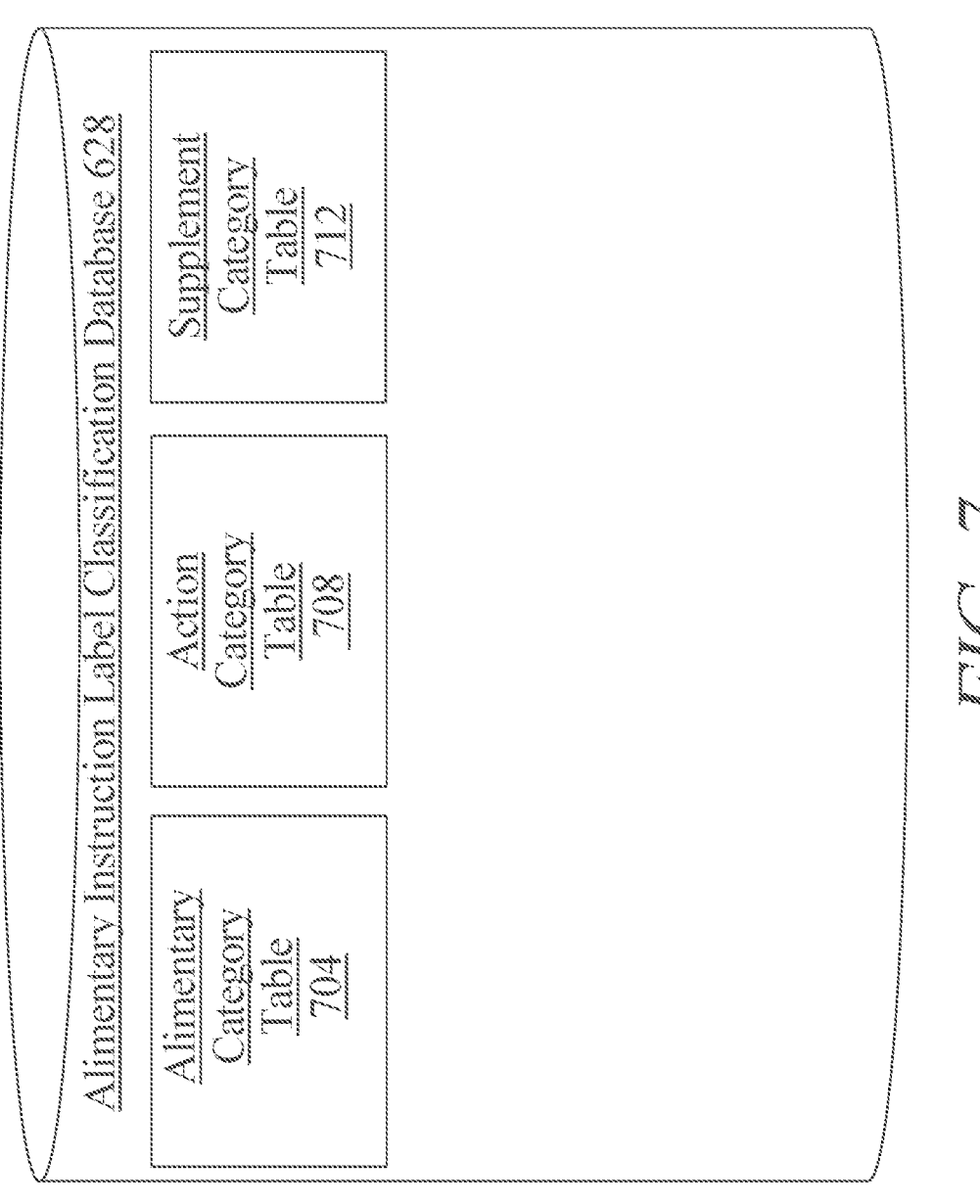
FIG. 7 is a block diagram illustrating an exemplary embodiment of an alimentary instruction label classification database.

Referring now to FIG. 7, an exemplary embodiment of an alimentary instruction label classification database 628 is illustrated. Alimentary instruction label classification database 628 may operate on the server 102. Alimentary instruction label classification database 628 may be implemented as any database and/or datastore suitable for use as a database. One or more database tables in alimentary instruction label classification database 628 may include, without limitation, an alimentary category table 704; which may associate an alimentary instruction label with one or more categories of nutritional properties, ingredients, foodstuffs, or the like. One or more database tables in alimentary instruction label classification database 628 may include, without limitation, an action category table 708, which may describe one or more categories of self-fulfillment actions, such as grocery shopping for ingredients either online or in person, preparing a meal at home, or the like, to which a given alimentary instruction may belong. One or more database tables in alimentary instruction label classification database 628 may include, without limitation, a supplement table 712, which may describe a supplement that relates to a dietary request, such as a grain free diet with a recommendation for fiber supplementation or a vegetarian diet with a recommendation for B vitamin supplementation.

Figure 8:
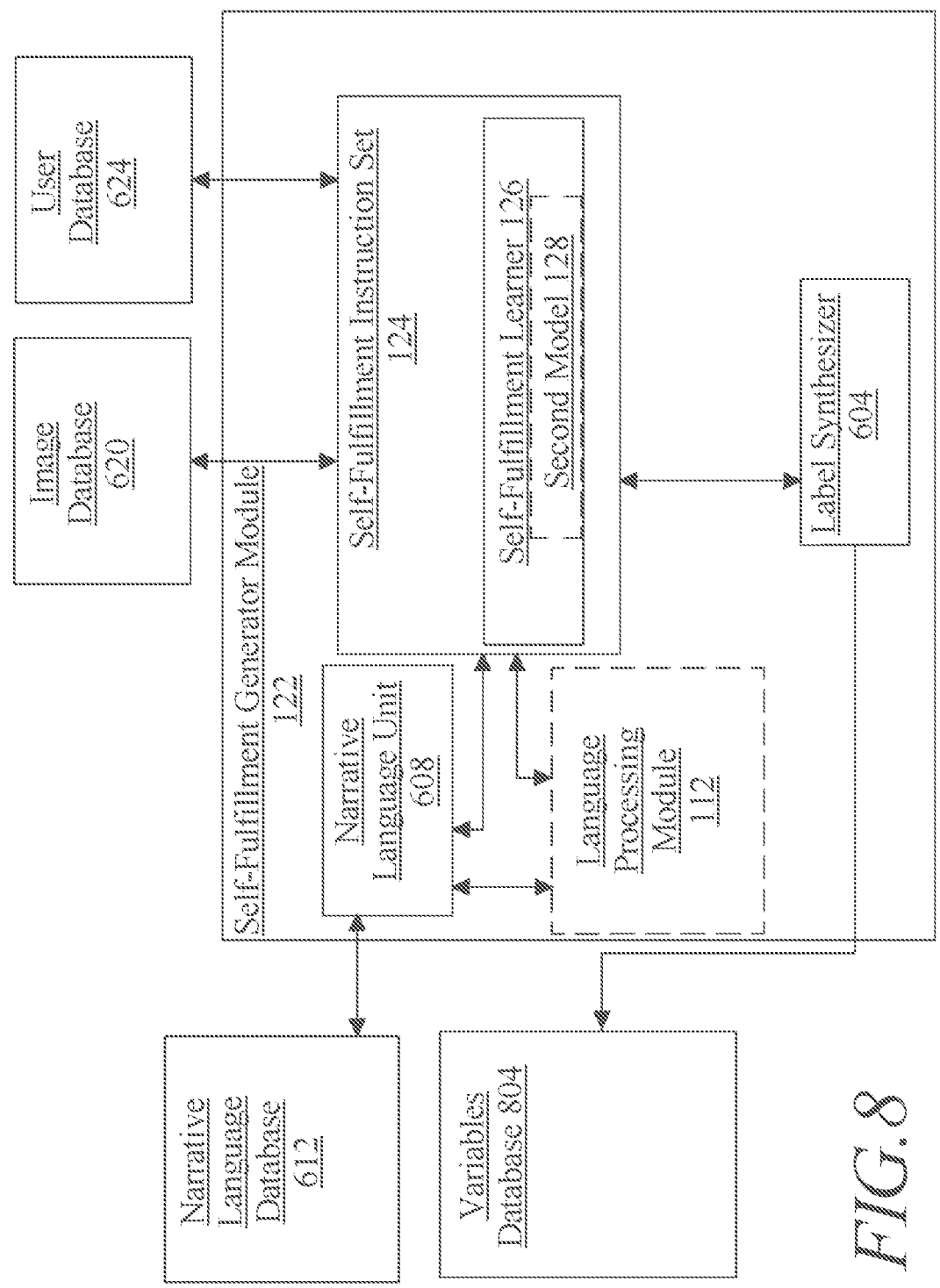
FIG. 8 is a block diagram illustrating an exemplary embodiment of a self-fulfillment generator module.

Referring now to FIG. 8, an exemplary embodiment of self-fulfillment instruction set generator module 122 is illustrated. Self-fulfillment generator module 122 may include any hardware or software module. Self-fulfillment generator module 122 is configured to generate at least a self-fulfillment instruction set as a function of the at least an alimentation instruction set and containing at least a self-fulfillment action. Self-fulfillment instruction set 124 may include any of the self-fulfillment instruction sets as described above in reference to FIG. 1. Self-fulfillment instruction set 124 may be generated by self-fulfillment learner 126 utilizing machine-learning as described in more detail below in reference to FIG. 8. Self-fulfillment generator module may perform supervised machine-learning, unsupervised machine-learning, and/or lazy learning processes. In an embodiment, self-fulfillment generator module 122 may generate self-fulfillment instruction set utilizing a loss function analysis as described above in more detail in reference to FIG. 1. Self-fulfillment generator module 122 may utilize variables database 804 to generate loss function using different variables. Variables that may be utilized and stored within variables database 804 are described in more detail below in reference to FIGS. 9-10. Self-fulfillment generator module 122 may contain label synthesizer 604, which may include any of the label synthesizer 604 as described above in more detail in reference to FIG. 6. Narrative language unit 608 may be utilized to analyze one or more alimentary instruction sets and generate them into narrative language. This may be performed utilizing any of the methodologies as described above in reference to FIG. 6, and may include consulting narrative language database 612. Self-fulfillment generator module may consult image database 620 and/or user database 624.

Figure 9:
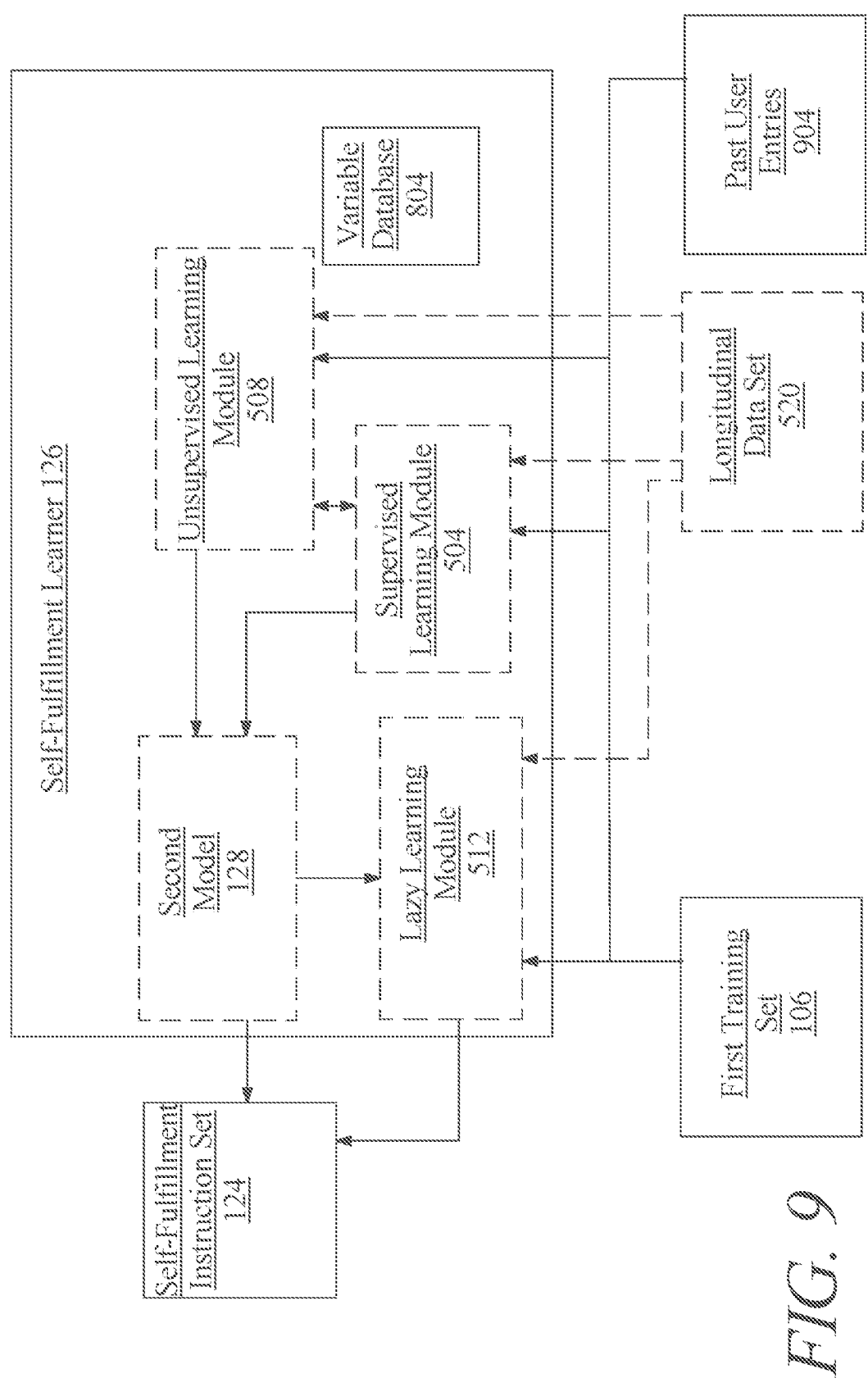
FIG. 9 is a block diagram illustrating an exemplary embodiment of a self-fulfillment learner and associated system elements.

Referring now to FIG. 9, an exemplary embodiment of self-fulfillment learner 126 is illustrated. Self-fulfillment learner 126 may be configured to perform one or more supervised learning processes, as described above; supervised learning processes may be performed by a supervised learning module 504 executing on server 102 and/or on another computing device in communication with server 102, which may include any hardware or software module. For example, supervised learning algorithm may use alimentary instruction set as inputs, and user entries containing an alimentary self-fulfillment action as outputs and/or self-fulfillment instruction set as output and a scoring function representing a desired form of relationship to be detected between alimentary self-fulfillment action and alimentary instruction sets; scoring function may, for instance, seek to maximize the probability that a given alimentary instruction set is associated with an alimentary self-fulfillment action. In yet another non-limiting example, supervised learning algorithm may use self-fulfillment instruction set as inputs and user entries containing an alimentary self-fulfillment action as output and a scoring function representing a desired form of relationship to be detected between alimentary self-fulfillment action and self-fulfillment instruction sets; scoring function may, for instance seek to maximize the probability that a given self-fulfillment instruction set is associated with an alimentary self-fulfillment action. In an embodiment, one or more supervised machine-learning algorithms may be restricted to a particular domain; for instance, a supervised machine-learning process may be performed with respect to a given set of parameters and/or categories of self-fulfillment instruction sets that have been suspected to be related to a given set of user entries containing an alimentary self-fulfillment action for instance because the user entries containing an alimentary self-fulfillment action corresponding to the self-fulfillment instruction set are hypothesized or suspected to be linked to a field of actions or group of actions. For example, a particular set of self-fulfillment instruction sets relating to obtaining groceries such as creating grocery lists, ordering groceries, shopping for groceries, and putting groceries away may all relate to obtaining groceries, and a supervised machine-learning process may be performed to relate these self-fulfillment actions to those contained within a self-fulfillment instruction set.

With continued reference to FIG. 9, self-fulfillment learner 126 may perform one or more supervised machine-learning processes as described above, including a loss function analysis utilizing linear regression based on past user interactions with system 100, such as information collected from user entries and alimentary instruction sets and/or self-fulfillment instruction sets. Loss function analysis may use supervised machine-learning processes and algorithms to iterate and converge towards a minimum where further tweaks to the variables produce little or zero changes in the loss or convergence by optimizing weights utilized by machine learning algorithms. Self-fulfillment learner 126 may utilize variables to model relationships between past interactions between a user such as previously generated user entries and self-fulfillment instruction sets and/or alimentary instruction sets. Loss function analysis may utilize variables that may be weighted and adjusted to predict outcomes. Variables may be personalized based on user inputs and weighted based on user inputs. For example, a user may weight one variable as being more important than another while another user may attribute equal weight to each variable. Variables may be contained with a variables database 804 as described in more detail below in reference to FIG. 10. Loss function analysis may utilize past user entries 904 to generate outputs such as self-fulfillment instruction set 124. Past user entries 904 may include any information pertaining to user's previous interactions with system 100. Past user entries 904 may include for example, previous user entries containing self-fulfillment actions, previous self-fulfillment instruction sets generated for a user, previous and/or previous alimentary instruction sets generated for a user.

With continued reference to FIG. 9, self-fulfillment learner 126 may utilize linear loss function algorithms customized around a user and based on user entries and past user performances to more accurately generate an alimentary instruction set 120 for a user, a self-fulfillment instruction set 124 for a user, and/or to update information and training sets utilized by server 102 and/or any modules operating on server 102. Loss function algorithms may utilize weighted variables customized to a user. Loss function algorithms may minimize distance between variables and may seek to minimize distance variable to variable. In an embodiment, after a user has submitted a user entry, the loss function may be re-run and updated. For example, if a user found a certain ingredient at a grocery store then self-fulfillment instruction set may be re-generated to update based on this development. Loss function algorithms may utilize weighted variables that are customized to a user. For example, user entries that contain trends and patterns as to self-fulfillment actions may be utilized by self-fulfillment learner to generate self-fulfillment instruction sets based on user trends and patterns to self-fulfill. For example, a user who enters user entries that show a frequency of cooking meals at home may be utilized by self-fulfillment learner 126 to generate self-fulfillment instruction sets that include recipes for the user or suggestions as to potential new ingredients to try. In yet another non-limiting example, a user who enters user entries that show a frequency of eating out at restaurants may be utilized by self-fulfillment learner 126 to generate self-fulfillment instruction sets that contain very basic recipes to prepare at home or that contain recommendations as to where a user can buy a meal on the go in user's area.

Figure 10:
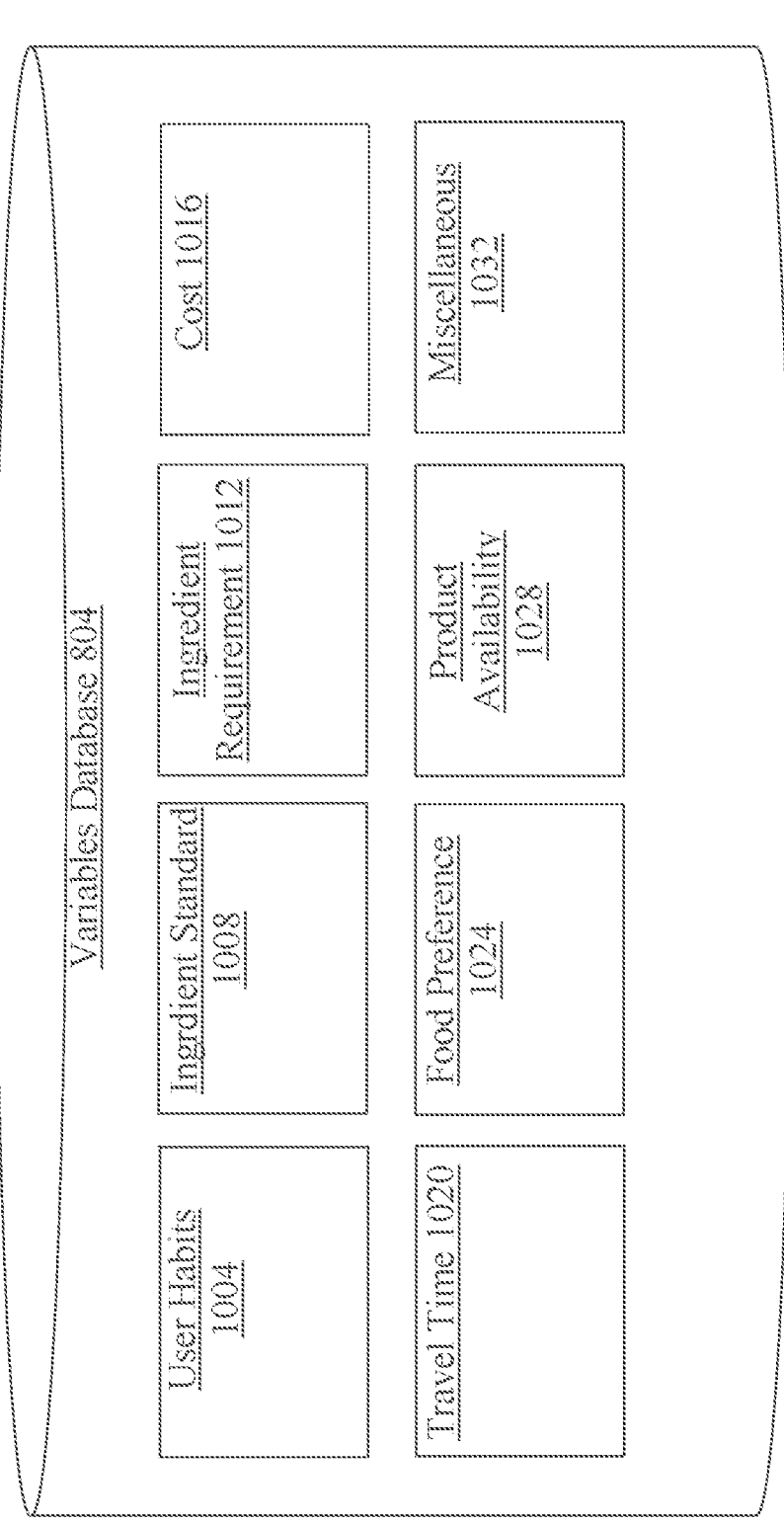
FIG. 10 is a block diagram illustrating an exemplary embodiment of a variables database.

Referring now to FIG. 10, an exemplary embodiment of variables database 804 is illustrated. Variables database 804 may be implemented as any database and/or datastore suitable for use as described above. One or more database tables in variables database 804 may include, without limitation, a user habits table 1004; user habits may contain information pertaining to ways in which a user self-fulfills such as a preference for eating out at restaurants, shopping for groceries, ordering meal kits, cooking at home, having a chef prepare meals, and the like. One or more database tables in variables database 804 may include without limitation, an ingredient standard table 1008; ingredient standard table 1008 may contain information relating to quality of food that a user typically consumes, such as a preference for organic produce, wild raised seafood, sustainably grown meats, free range poultry, locally sourced products and/or ingredients, products grown without the use of pesticides and the like. One or more database tables in variables database 804 may include without limitation, an ingredient requirement table 1012; ingredient requirement table 1012 may include information pertaining to if a certain food or item fulfills an alimentary instruction set. For example, a product such as kale, spinach, and celery may be categorized as containing fulfilling an alimentary instruction set that includes consumption of raw foods and vegetables. One or more database tables in variables database 804 may include without limitation, cost table 1016; cost may include information relating to user cost preference; cost preference may include user preference for eating out at restaurants versus cooking at home, buying groceries at a store versus cost to have groceries delivered, cost for organic versus inorganic products, cost for buying groceries as compared to having meals delivered, user budget for nutrition and supplements, and the like. One or more database tables in variables database 804 may include without limitation, travel timetable 1020; travel time may include information relating to how far a user is willing to travel for nutrition such as for example the miles or minutes a user will drive in a car to a restaurant or grocery store. One or more database tables in variables database 804 may include without limitation, food preference table 1024; food preferences may include a user's preference to consume certain foods or food groups, such as for example a user's preference to consume chicken and beef but a dislike of plant proteins such as tofu and lentils. One or more database tables in variables database 804 may include without limitation, product availability table 1028; product availability may include information as to whether certain products, foods, meals, supplements and the like are available in certain geographical locations. For example, fish tacos may be available in Anchorage, Alaska but not in Little Rock, Arkansas, as hazelnuts may be bountiful in the Pacific Northwest but scarce in Anchorage, Alaska. One or more database tables in variables database 804 may include without limitation, miscellaneous table 1032; miscellaneous may include other variables that may be utilized but have not been discussed above.

Referring back now to FIG. 9, self-fulfillment learner 126 may perform one or more unsupervised machine-learning processes as described above, unsupervised processes may be performed by an unsupervised learning module 508 executing on server 102 and/or on another computing device in communication with server 102, which may include any hardware or software module. For instance and without limitation, self-fulfillment learner 126 may perform an unsupervised machine learning process on training set 104, which may cluster data of training set 104 according to detected relationships between elements of the training set 104, including for example relationships between user entries and alimentary instruction sets and/or self-fulfillment instruction sets; such information may then be combined with supervised machine learning results to add new criteria for self-fulfillment learner 126 to apply in relating between user entries and alimentary instruction sets and/or self-fulfillment instruction sets.

With continued reference to FIG. 9, self-fulfillment learner 126 may be configured to perform a lazy learning process as a function of training set 104 to examine relationships between user entries and alimentary instruction sets and/or self-fulfillment instruction sets. Lazy learning process may include any lazy learning process as described above. Lazy learning processes may be performed by a lazy learning module 512 operating on server 102 and/or on another computing device in communication with server 102, which may include any hardware or software module.

Figure 11:
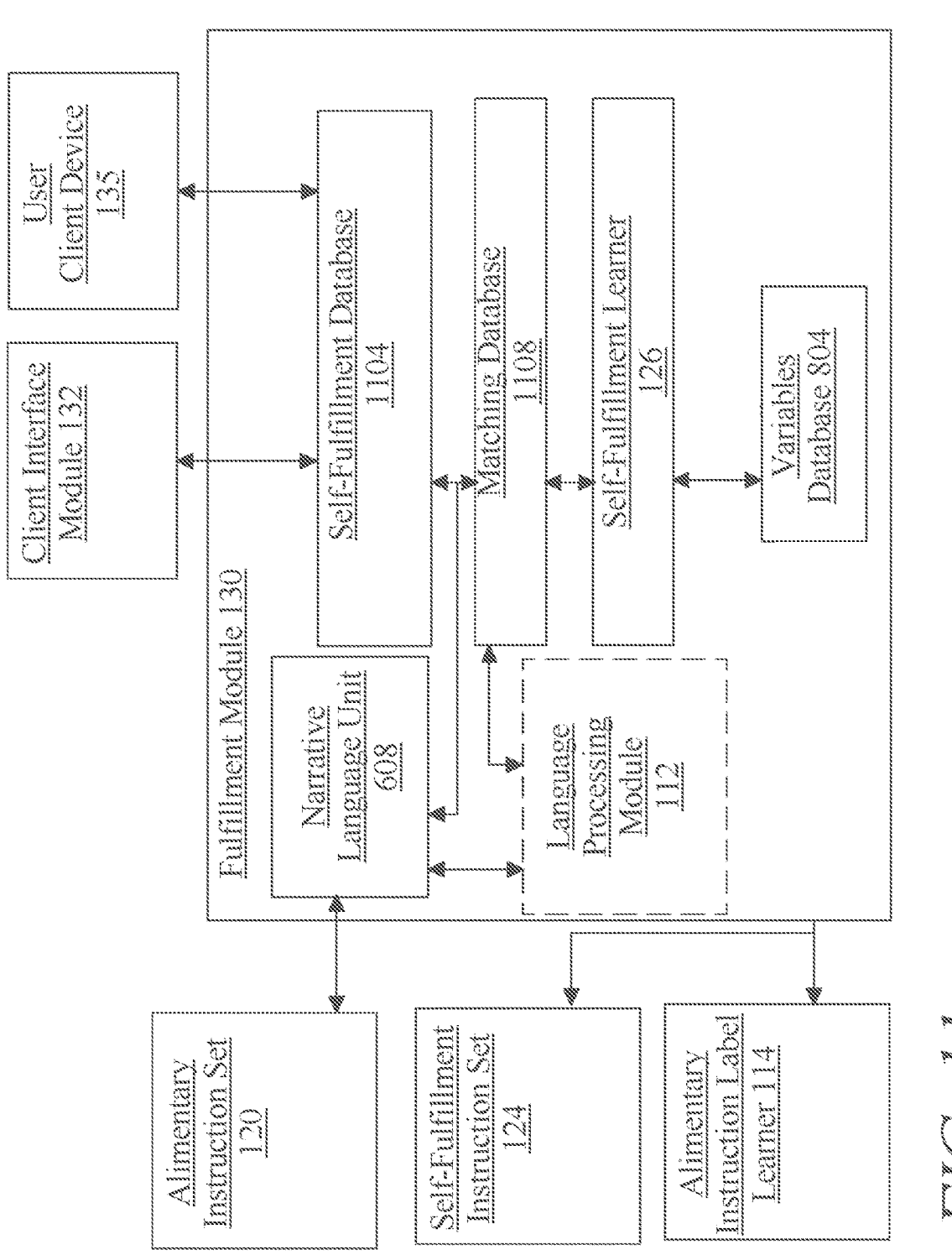
FIG. 11 is a block diagram illustrating an exemplary embodiment of a fulfillment module.

Referring now to FIG. 11, an exemplary embodiment of fulfillment module 130 is illustrated. Fulfillment module 130 may be designed and configured to receive a user entry containing an alimentary self-fulfillment action. Fulfillment module 130 may receive a user entry containing an alimentary self-fulfillment action from user client device 134 and/or through client interface module 132. Self-fulfillment action may include a description, photograph, selection, choice, and the like describing an action a user engaged in to self-fulfill alimentary instruction set 120. Action may include any steps, effort, and/or tasks that a user engage in to self-fulfill alimentary instruction set. Action may include for example, making a grocery list, shopping for supplements, preparing a meal kit, grabbing take out at a restaurant, purchasing a takeaway meal at a grocery store or meal delivery kitchen and the like. In an embodiment, self-fulfillment action may include an action as recommended by self-fulfillment instruction set and/or be related to an action as recommended by self-fulfillment instruction set. For example, self-fulfillment instruction set may recommend an action such as cooking a recipe containing wild salmon and broccoli rabe. Self-fulfillment action may include an action user took such as purchasing wild salmon at a grocery store or ordering a takeout meal that contained wild salmon and broccoli rabe.

With continued reference to FIG. 11, fulfillment module 130 may contain self-fulfillment database 1104. Self-fulfillment database 1104 may contain different database tables as described below in more detail in FIG. 13, that user entry containing an alimentary self-fulfillment action may be matched with to discover how user's behaviors are contributing to or hurting a user's dietary request. For example, a user may generate a dietary request for a gluten free diet as part of an elimination diet. User entries describing self-fulfillment actions over a period of time may then be matched against database tables located within self-fulfillment database 1104 to examine how user's actions have contributed to helping or hurting a user in following a gluten free diet.

With continued reference to FIG. 11, fulfillment module 130 may contain matching database 1108. Matching database 1108 may include different database tables as described below in more detail in FIG. 12. User entries containing alimentary self-fulfillment action may be matched utilizing matching database 1108 and/or self-fulfillment database

1104. User entries may be received by fulfillment module 130 as either textual entries such as a description of what a user consumed or purchased, graphical entries such as an upload of a meal user ate at a restaurant, and/or by user selection whereby user may select some type of self-fulfillment action from a predetermined list or chart. In an embodiment, user may select a self-fulfillment action from a list, such as one containing actions and/or recommendations from self-fulfillment instruction set. For example, self-fulfillment instruction set may contain a list of 3 options such as a new recipe user could cook, a recommended meal a user could consume, or a grocery store where a user could purchase groceries at. User may then select which of those 3 options user performed if any. In an embodiment, user may provide comments or edit selections such as if instead of consuming salmon and broccoli rabe as recommended by self-fulfillment instruction set 124, user instead consumed salmon and spinach. User entry may then be matched against a table contained within self-fulfillment database 1104 to examine how user entry may affect user's dietary request. For example, user entry containing repetitive self-fulfillment actions such as consuming fried foods may negatively affect user's dietary request for a grain free diet. In yet another non-limiting example, user entry containing a self-fulfillment action such as eating beans and rice for breakfast may positively affect a user's request to follow a vegetarian diet. Fulfillment module 130 may utilize matching to compare user entry containing an alimentary self-fulfillment action to at least an alimentary instruction set. For example, an alimentary self-fulfillment action containing a list of meals user consumed in one day may be matched against alimentary instruction set to determine if user consumed recommended nutrients or supplements as provided for by alimentary instruction set and/or if user consumed foods user may have eliminated with a dietary request. For example, a user entry containing a home cooked meal that contained miso cod over buckwheat with a side salad may be matched against alimentary instruction set to determine if a user entry contains gluten. In yet another non-limiting example, user entry such as a grocery list of purchased groceries from an online grocery store may be matched against alimentary instruction set to determine if user's purchases fulfill recommended nutrient and dietary recommendations contained within alimentary instruction set. In an embodiment, alimentary instruction set may be modified as a function of user entry. For example, an alimentary instruction set may be updated to contain new recommendations for foods or meals that a user may wish to consume based on previous user entries. For example, a user who may frequently generate a user entry with meals containing buckwheat while on a gluten free diet may receive alimentary instruction sets with new recipes containing buckwheat. In yet another non-limiting example, alimentary instruction set may be updated as a function of user entry such as for example, in the winter time when a user may consume heavier foods containing more starches when it is cooler outside as compared to the summer time when a user may consume light foods such as salads and soups.

Figure 12:
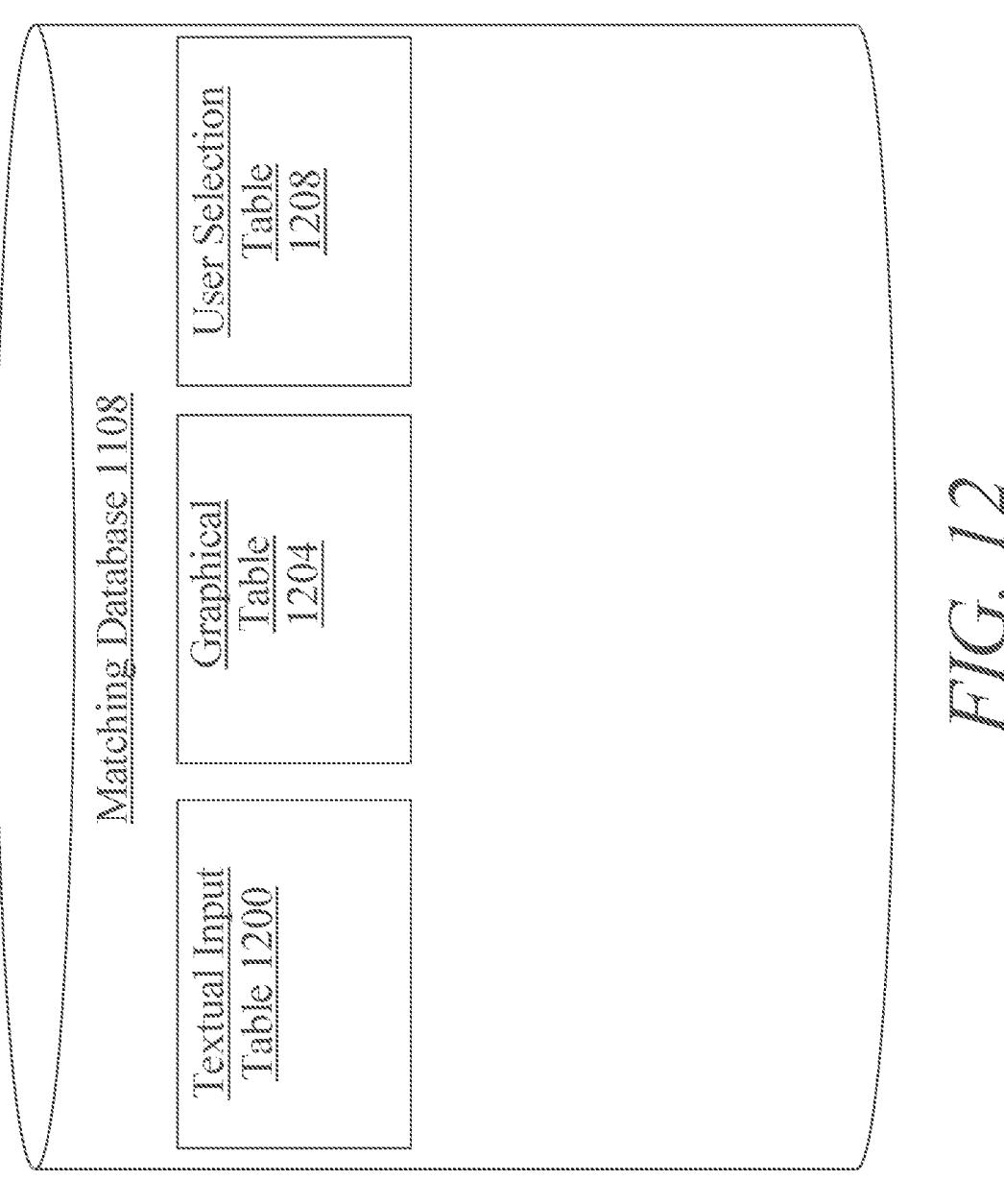
FIG. 12 is a block diagram illustrating an exemplary embodiment of a matching database.

Referring now to FIG. 12, an exemplary embodiment of matching database 1108 is illustrated. Matching database 1108 may be implemented as any database and/or datastore suitable for use as described above. Matching database 1108 may include one or more tables containing one or more categories of user entries that may be matched against information contained within self-fulfillment database 1104 such as by fulfillment module 130. One or more database tables in matching database 1108 may include textual input table 1200, which may include user entries containing text such as a word or string of words, description, or paragraph describing user's alimentary self-fulfillment actions. One or more database tables in matching database 1108 may include graphical table 1204, which may include user entries containing graphics such as pictures, images, and/or graphical representations describing user's alimentary self-fulfillment actions. One or more database tables in matching database 1108 may include user selection table 1208, which may include user entries that a user has selected from a list or drop-down menu.

Referring back now to FIG. 11, fulfillment module 130 may use machine-learning such as by self-fulfillment learner 126 to utilize user entries in a feedback mechanism to provide subsequent alimentary instruction set 120, self-fulfillment instruction set 124, and/or provide captured data to server 102 to update training set 104. Fulfillment module 130 may utilize supervised and/or unsupervised machine-learning processes as described above in reference to FIG. 1 and FIG. 18. Fulfillment module 130 may utilize lazy learning processes as described above in reference to FIG. 1 and FIG. 18.

Figure 13:
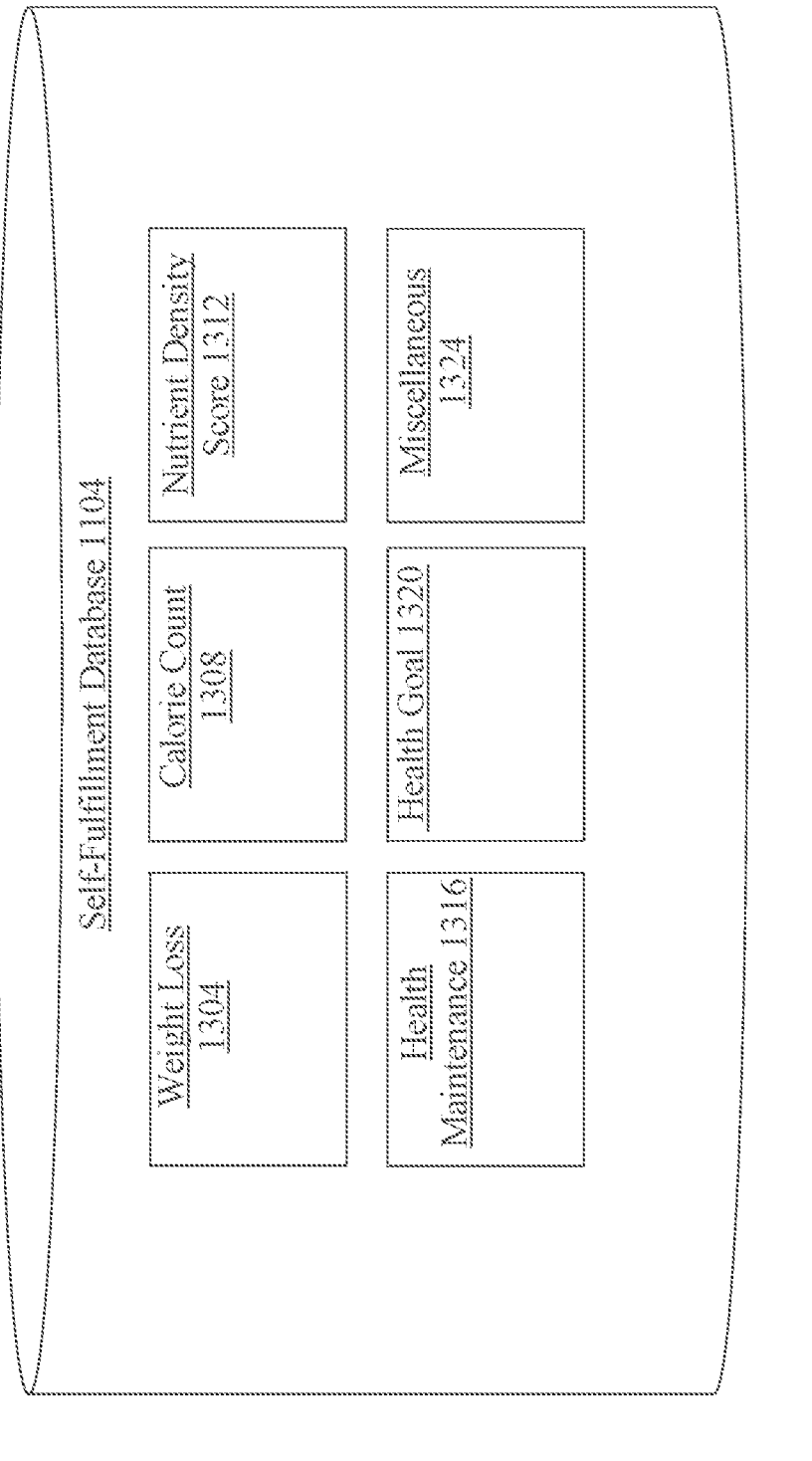
FIG. 13 is a block diagram illustrating an exemplary embodiment of a self-fulfillment database.

Referring now to FIG. 13, an exemplary embodiment of self-fulfillment database 1104 is illustrated. Self-fulfillment database 1104 may be implemented as any database and/or datastore suitable for use as described above. Self-fulfillment database 1104 may contain information examining how user's self-fulfillment selections as transmitted to server 102 and processed by fulfillment module 130 have affected a user's ability to achieve and/or sustain user dietary request. One or more database tables in self-fulfillment database 1104 may include, weight loss table 1304; weight loss may include information describing how user's self-fulfillment options and selections have attributed to weight loss if any over a specific period of time. One or more database tables in self-fulfillment database 1104 may include calorie count table 1308, calorie count may include information describing how user's self-fulfillment options and selections have attributed to certain calorie requirements such as those recommended by a nutritionist or dietician. One or more database tables in self-fulfillment database 1104 may include nutrient density score table 1312, nutrient density score may include information describing how user's self-fulfillment options and selections have led to nutrient dense selections such as for example the nutrient density score of consuming a home cooked meal with little oil versus a friend chicken sandwich from a fast food restaurant. One or more database tables in self-fulfillment database 1104 may include health maintenance table 1316, health maintenance may include information describing how user's self-fulfillment options and selections have aided a user in maintaining user's health. User's health may include maintaining a certain status or level of health, such as for example achieving a goal body mass index (BMI) for somebody of user's age or se. One or more database tables in self-fulfillment database 1104 may include health goal table 1320, which may include information describing how user's self-fulfillment options and selections helped or hurt a user in achieving a particular health goal. Health goal may include any goal a user may set as it relates to user's health, such as for example, cooking three meals each week at home or ordering low carbohydrate meals at restaurants. One or more database tables in self-fulfillment database 1104 may include miscellaneous table 1324, which may contain any other information relating a user's self-fulfillment options and selections that may aid or derail a user from achieving user's dietary request.

Figure 14:
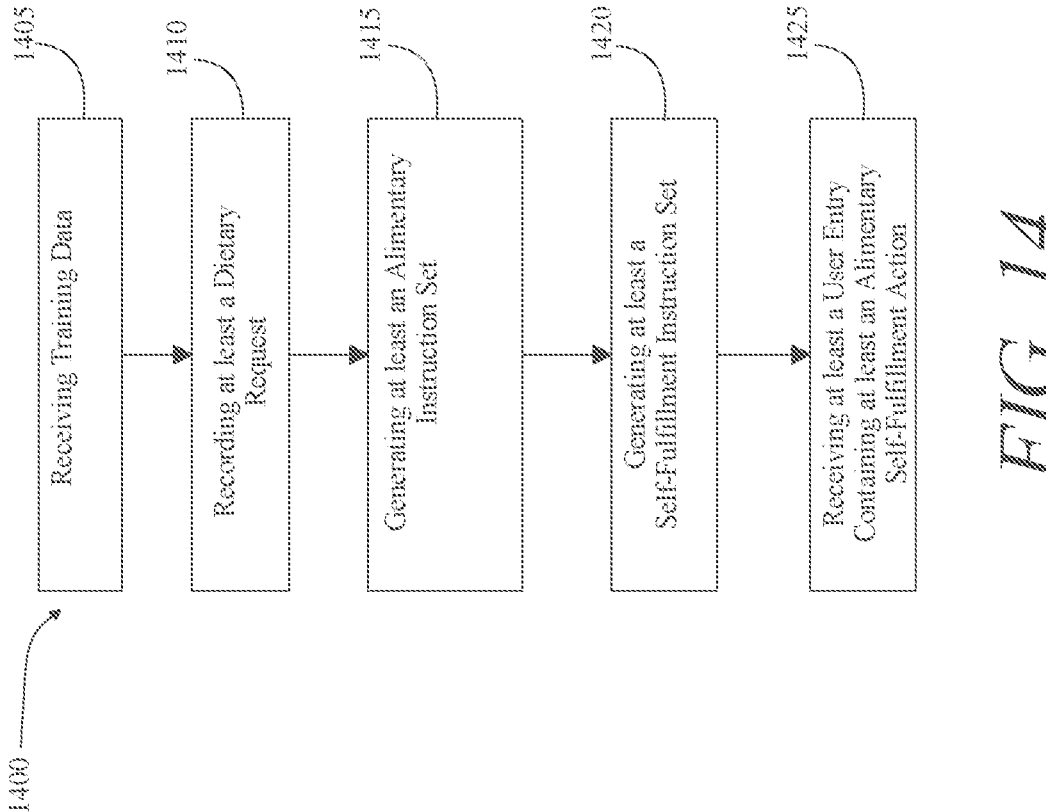
FIG. 14 is a flow diagram illustrating an exemplary embodiment of a method of self-fulfillment of a dietary request.

Referring now to FIG. 14, an exemplary embodiment of a method of self-fulfillment of a dietary request 1400 is illustrated. At step 1405 at least a server receives training data. Receiving training data includes receiving a training set including a plurality of data entries, each data entry of the plurality of data entries including at least an element of dietary request data and at least a correlated first alimentary label. Receiving training data may be performed by any of the methodologies a described in FIGS. 1-14. Training data may include any of the training data as described in FIGS. 1-14.

With continued reference to FIG. 14, at step 1410 the at least a server receives at least a dietary request from a user device. Dietary requests may include any of the dietary requests as described above in reference to FIGS. 1-14. In an embodiment, at least a dietary request may be received from a computing device. For example, at least a computing device may generate a nutrition plan containing food, diet, and/or supplementation recommendations. In such an instance, computing device may generate at least a dietary request as a function of a nutrition plan. In such an instance, at least a server may receive at least a dietary request from a computing device.

With continued reference to FIG. 14, at step 1415 the at least a server generates at least an alimentary instruction set as a function of the at least a dietary request from the user device and the training data. Generating alimentary instruction set may include performing at least a machine-learning algorithm as a function of the training data and the at least a dietary request. Machine-learning algorithm may include any of the machine-learning algorithms as described above in reference to FIGS. 1-14. In an embodiment, alimentary instruction set may be generated as a function of at least a datum of user data including a user preference. For example, alimentary instruction set generator module may receive a user preference for a particular type of food or food groups. For example, a user may prefer to consume meats such as veal, lamb, and pork but have an aversion to chicken. In yet another non-limiting example, a user may have a preference for grilled chicken but have an aversion to baked chicken.

With continued reference to FIG. 14, at step 1420 the at least a server generates at least a self-fulfillment instruction set as a function of the at least an alimentary instruction set containing at least a self-fulfillment action. Self-fulfillment instruction set may include any of the self-fulfillment instruction sets as described above in reference to FIGS. 1-14. Self-fulfillment action may include any of the self-fulfillment actions as described above in reference to FIGS. 1-14. In an embodiment, self-fulfillment action may include any step, action, and/or process a user may take to engage in partake in initiating at least a self-fulfillment instruction set. In an embodiment, self-fulfillment instruction set may be generated as a function of user geo-location. For example, self-fulfillment instruction set may contain ways in which a user may self-fulfill an alimentary instruction set such as groceries a user may shop for at a local grocery store in user's location, or a restaurant a user may purchase a meal at located within a certain geographical distance of a user. In an embodiment, a user may enter details such as how many miles a user may be willing to travel to self-fulfill. In an embodiment, self-fulfillment instruction set may be generated utilizing a loss function of user specific variables and minimizing the loss function. Variables contained within the loss function may include an ingredient standard request which may contain information pertaining to standards a user prefers as to food, nutrition, and supplements, such as a preference for locally grown produce and/or free range poultry. This may include any of the ingredient standard requests as described above in more detail above in reference to FIGS. 8-10. In an embodiment, variable may include an ingredient requirement request as described above in reference to FIGS. 8-10. This may include for example, information pertaining to how an ingredient may complete a dietary request. In an embodiment, after a user has implemented one step of the self-fulfillment instruction set, the loss function may be re-run to update the self-fulfillment instruction set. In an embodiment, the self-fulfillment instruction set may be generated as a function of user geolocation. In an embodiment, self-fulfillment instruction set may be transmitted to a user device.

With continued reference to FIG. 14, at step 1425 the at least a server receives a user entry containing an alimentary self-fulfillment action. Alimentary self-fulfillment action may include any of the alimentary self-fulfillment actions as described above in reference to FIGS. 1-14. Reception of self-fulfillment action may be utilized to track a user location and match alimentary instruction sets and/or self-fulfillment instruction sets to a user. For example, if a user decides to take action regarding a self-fulfillment instruction set such as following directions to a specific grocery store, then user entry may be analyzed and matched to inquire if user actually purchased items relating to alimentary instruction set. In an embodiment, a user may pull up a screen that may allow a user to enter purchased ingredients or scan barcodes pertaining to specific ingredients. Alimentary self-fulfillment action may be received using any of the methodologies as described herein. In an embodiment, user entry containing alimentary self-fulfillment action may be matched by fulfillment module 130. Matching may include any of the matching methodologies as described above in reference to FIGS. 11-13. Matching may include matching a user entry containing an alimentary self-fulfillment action to at least an alimentary instruction set and/or to at least a self-fulfillment instruction set. In an embodiment, self-fulfillment action may include textual entries, graphics such as photographs, and/or user selection from a drop-down menu and may be received using any methodologies as described herein. In an embodiment, alimentary instruction set may be modified as a function of user entry. For example, an alimentary instruction set that contains a recommendation to consume kale may be modified after a user has entered user entries that never contain consumption of such foods and as such, other greens such as spinach or butter lettuce may be recommended if appropriate. In yet another non-limiting example, alimentary instruction set that recommends a user to consume buckwheat may be updated to recommend consumption of other grains including for example, quinoa, and long grain rice if for example a user has repeatedly consumed buckwheat over a certain period of time.

Figure 15:
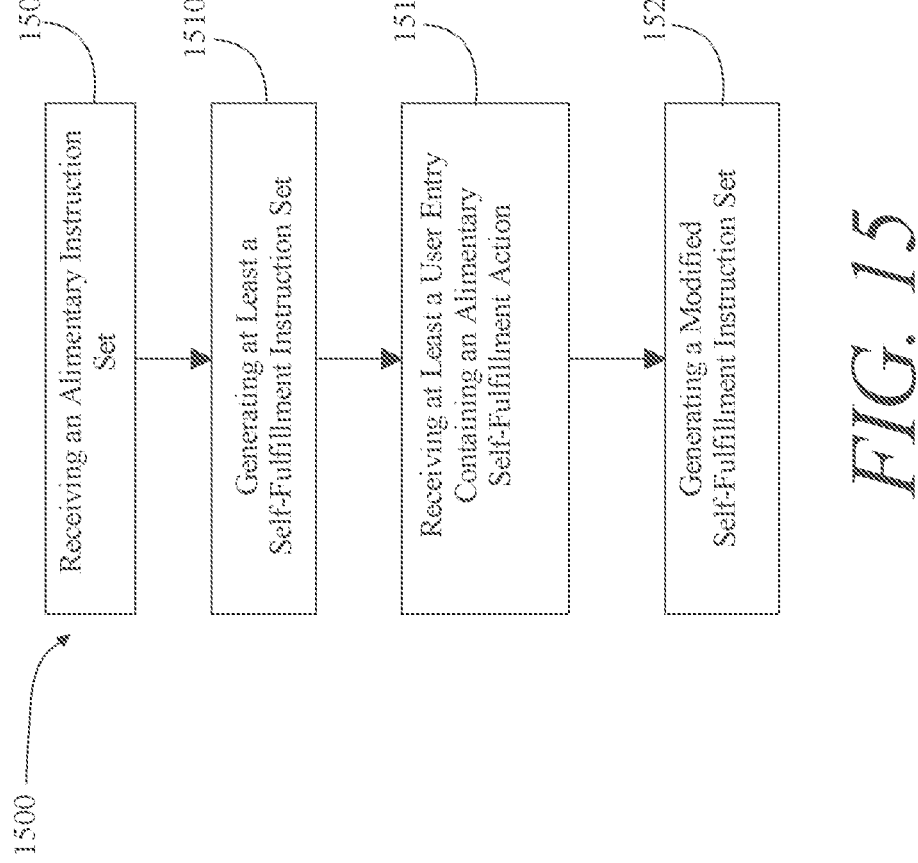
FIG. 15 is a flow diagram illustrating an exemplary embodiment of a method of self-fulfillment of a dietary request.

Referring now to FIG. 15, an exemplary embodiment of a method 1500 of self-fulfillment of a dietary request is illustrated. At step 1505, at least a server receives an alimentary instruction set as a function of a user dietary request; this may be implemented, without limitation, as described above in reference to FIGS. 1-14. For instance, and without limitation, receiving the alimentary instruction set may include receiving at least a user dietary request and generating the alimentary instruction set as a function of the at least a user dietary request, which may be accomplished without limitation as described above in reference to FIGS. 1-14.

At step 1510, at least a server generates at least a self-fulfillment instruction set, the self-fulfillment instruction set including a data structure identifying a plurality of self-fulfilling actions a user can take to self-fulfill a suggested nourishment requirement, as a function of at least a self-fulfillment action; this may be implemented, without limitation, as described above in reference to FIGS. 1-14. For instance, and without limitation, generating the at least a self-fulfillment instruction set may include receiving training data including a plurality of data entries, each data entry of the plurality of data entries including at least an alimentary instruction and at least a correlated self-fulfillment action datum, training a machine-learning model as a function of the training data, and generating the at least a self-fulfillment instruction set as a function of the alimentary instruction set and the machine-learning model.

In some embodiments, and with continued reference to FIG. 1500, generating the at least a self-fulfillment instruction set may include generating a query as a function of at least an instruction of the self-fulfillment instruction set, querying a web index as a function of the query, receiving a search result corresponding to the query, and modifying the at least an instruction as a function of the search result. Query may include, without limitation any self-fulfillment instruction and/or element thereof; for instance, a query may include one or more ingredients, meals, elements of kitchenware, or the like usable to perform a self-fulfillment as described above. A "web index," as used in this disclosure, is a data structure linking one or more words, phrases, keywords, or other terms usable as part of a search query to one or more network addresses such as Internet Protocol (IP) addresses, uniform resource locators (URLs) or the like. Web index may be a general-purpose web index, or may be a cohort-specific web index to which user may be classified according to one or more classification processes. A search result from a query of a web index may include any network addresses. Web indices and/or cohort-specific indices may be implemented, without limitation, in any way disclosed in U.S. Nonprovisional application Ser. No. 16/727,113, filed on Dec. 26, 2019 and entitled "METHODS AND SYSTEMS FOR PHYSIOLOGICALLY INFORMED NETWORK SEARCHING," the entirety of which is incorporated herein by reference. Modification of self-fulfillment instruction set as a function of search result may include, without limitation, appending a network address to one or more self-fulfillment instructions that were used to generate query, adding locations of stores or other suppliers, directions thereto, map data, or the like to the self-fulfillment instruction set, or the like. For instance, a list of addresses of stores where a given ingredient may be found may be returned, along with links to directions for navigation thereto. Persons skilled in the art, upon reviewing the entirety of this disclosure, will be aware of various forms of information that may be added to self-fulfillment instruction set as a function of search results.

Still referring to FIG. 15, generation of an index, and/or generation of one or more generation of cohort specific indices as described in further detail below, may be performed using a web crawler. A "web crawler," as used in this disclosure, is a program that visits content at URLs and extracts keywords and/or key phrases from content. In an embodiment, web crawler may assess each visited page initially by inspection of a limited number of fields such as <meta> tags, titles, and/or other fields indicative of likely contents, and/or some initial quantity of text received from a site. For instance, a web crawler may check for standard filename robots.txt, addressed to it, which may contains directives for web crawler, telling it which pages to crawl. Web crawler may send certain information back to be indexed, such as the titles, page content. JavaScript, Cascading Style Sheets (CSS), headings, or metadata in HTML meta tags. After a certain number of pages crawled, amount of data indexed, or time spent on the website, which may be weighted and/or determined based on heuristic as described in further detail below, web crawler may proceed to a new URL. Web crawler for a given cohort may, without limitation, calculate a cohort relevance heuristic using initially analyzed text, and compare resulting score to a threshold, where failing to meet threshold may indicate that content is insufficiently relevant to warrant further analysis. Heuristic output may be combined with output of one or more additional algorithms for determining whether to inspect content at a URL further; for instance relevance score generated using heuristic may be used to weight a relevance score generated by other processes.

In an embodiment, and continuing to refer to FIG. 15, where a feature learning process or the like is used to generate new clusters and/or cohorts as described in this disclosure, computing device and/or other device may create a new index for each new cohort; new index may be initially populated, without limitation, using entries from indices of one or more most proximate cohorts, where proximity may be determined using proximity determination of classifiers and/or feature learning algorithms 128 as described above. Each crawling and/or index generation step and/or process as described above may be performed iteratively, with index entries updated and/or replaced periodically; thus each cohort index may continuously refine its degree of relevance to its corresponding cohort of users.

Still referring to FIG. 15, querying the web index may include classifying the user to a physiologically linked web index and/or cohort-specific web index, and querying the physiologically linked web index. This may be performed, without limitation, using an index classifier. In some embodiments, index training data, defined as training data used to generate index classifier, may include, without limitation, a plurality of data entries, each data entry including one or more elements of physiological data such as biological extractions, and one or more correlated user cohort labels, where user cohort labels and associated physiological profiles may be identified using feature learning algorithms as described below. Index training data and/or elements thereof may be added to, as a non-limiting example, by classification of multiple users' physiological data to cohort labels using one or more classification algorithms.

Still referring to FIG. 15, a computing device may be configured to generate index classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)÷P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 15, computing device may be configured to generate index classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 15, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of user-entered words and/or phrases, a plurality of attributes of a media item, such as spoken or written text, objects depicted in images, metadata, or the like, to clusters representing themes.

In an embodiment, and still referring to FIG. 15, computing device, and/or a device generating index classifier, may generate new cohort labels using a feature learning algorithm. A "feature learning algorithm," as used herein, is a machine-learning algorithm that identifies associations between elements of data in a training data set, where particular outputs and/or inputs are not specified. For instance, and without limitation, a feature learning algorithm may detect co-occurrences of sets of physiological data, as defined above, with each other. As a non-limiting example, feature learning algorithm may detect co-occurrences of gene combinations, as defined above, with each other. Computing device may perform a feature learning algorithm by dividing physiological data from a given person into various sub-combinations of such data to create physiological data sets as described above, and evaluate which physiological data sets tend to co-occur with which other physiological data sets; for instance, where physiological state data includes genetic sequences, computing device may divide each genetic sequence into individual genes and evaluate which individual genes and/or combinations thereof tend to co-occur with which other individual genes, and/or other physiological data. In an embodiment, first feature learning algorithm may perform clustering of data.

Continuing refer to FIG. 15, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 15, computing device may generate a k-means clustering algorithm receiving unclassified physiological state data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related physiological data, which may be provided with user cohort labels; this may, for instance, generate an initial set of user cohort labels from an initial set of user physiological data of a large number of users, and may also, upon subsequent iterations, identify new clusters to be provided new user cohort labels, to which additional user physiological data may be classified, or to which previously used user physiological data may be reclassified.

With continued reference to FIG. 15, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $\text{argmin}_{c_i \in c} \text{dist}(c_i, x)^2$, where argmin includes argument of the minimum, $c_i$ includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \in x_i \in S_i^{xi}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 15, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set. Degree of similarity index value may indicate how close a particular combination of genes, negative behaviors and/or negative behavioral propensities is to being classified by k-means algorithm to a particular cluster. K-means clustering algorithm may evaluate the distances of the combination of genes, negative behaviors and/or negative behavioral propensities to the k-number of clusters output by k-means clustering algorithm. Short distances between a set of physiological data and a cluster may indicate a higher degree of similarity between the set of physiological data and a particular cluster. Longer distances between a set of physiological behavior and a cluster may indicate a lower degree of similarity between a physiological data set and a particular cluster.

With continued reference to FIG. 15, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a physiological data set and the data entry cluster. Alternatively or additionally k-means clustering algorithm may select a plurality of clusters having low degree of similarity index values to physiological data sets, indicative of greater degrees of similarity. Degree of similarity index values may be compared to a threshold number indicating a minimal degree of relatedness suitable for inclusion of a set of physiological data in a cluster, where degree of similarity indices falling under the threshold number may be included as indicative of high degrees of relatedness. The above-described illustration of feature learning using k-means clustering is included for illustrative purposes only, and should not be construed as limiting potential implementation of feature learning algorithms; persons skilled in the art, upon reviewing the entirety of this disclosure, will be aware of various additional or alternative feature learning approaches that may be used consistently with this disclosure.

In an embodiment, and still referring to FIG. 15, computing device and/or another device in communication therewith may generate an initial set of user cohort labels using an initial feature learning algorithm; for instance, an initial estimate number k of user cohort labels may be created, and feature learning algorithm may be performed to generate k clusters. This may be followed by performance of a classification algorithm; where a threshold number of physiological data sets does not converge within a threshold distance of any cluster according to the classification algorithm, device performing these processes may increment k by one or more integer values and perform feature learning algorithm a second time; this may be repeated until a threshold proportion of population of physiological data sets converges within a threshold distance of clusters under classification algorithm.

Further referring to FIG. 15, computing device and/or other device may follow a process for creation of new cohort labels, either initially or when index classifier is being run against newly submitted biological extractions. At step, computing device and/or other device may perform classification of one or more elements of physiological data and/or biological extractions as described above. At step, computing device and/or other device may record degree of convergence with existing clusters of each such biological extraction; if distances, such as average distances from cohort label clusters, are below a threshold level, process may return to classification with current cohort labels, for instance using new biological extractions or the like. Where a threshold population fails to converge within a threshold distance of existing clusters, k may be incremented at step and feature learning algorithm may be run at step to generate one or more new cohort labels, to which physiological data sets may be classified by running classification algorithm to generate an updated index classifier. Process may then return to classification and repeat determinations; k may be incremented, and feature learning performed, repeatedly, until convergence brings distances below a desired and/or recorded threshold level. System 100 may ensure by such a process that classification algorithm identifies cohorts closely related to a user; this may help to ensure that search results are closely tailored to a user based on biological extraction.

Referring again to FIG. 15, computing device is configured to output, from the index classifier, a physiologically linked web index. Index classifier may classify biological extraction to a cohort label using a classification algorithm as described above, for instance by identifying a cohort label associated with a cluster of physiological data sets having a greatest degree of similarity to biological extraction. In an embodiment, computing device may include additional physiological data associated with user, such as without limitation physiological data received in past biological extractions from user. Physiological data of each user may be stored, without limitation, in a user database, which may be implemented using any data structure suitable for implementation of web indices; user database may be located in memory of computing device and/or on another device in and/or in communication with system 100.

Still referring to FIG. 15, computing device is configured to generate, using the physiologically linked web index and the search query, a ranked search result. Search result may be retrieved from physiologically linked web index by submission of words and/or phrases as queries to physiologically linked web index; queries and results thereof may be processed in any manner suitable for queries of databases, data stores, and the like. Search result may take the form of a list of URLs returned in response to queries, for instance in the form of links to such URLs. Search result may be ranked. Entries in an index such as physiologically linked web index may have rankings associated therewith based on relevance to cohort, for instance using heuristics during crawling or index generation, as described below. A rank of an index entry may be represented by a first numerical variable, which may be referred to herein as an "index rank." Ranking may alternatively or additionally be determined according to a number of keyword and/or phrase detections in content at a give URL; for instance, a numerical variable referred to herein as a "relevance rank" may be increased for URLs in search results having more total appearances of keywords and/or phrases, more clustering of keyword and/or phrases together, or the like. Keywords themselves may be hierarchically ordered, such that each keyword may have a relevance score; a "keyword score" numerical variable for each search result may aggregate keyword scores of keywords from and/or matching search query 140 that are found in contents at the search result. An "inverted index score" may alternatively or additionally generate a score for a search result using the text. A "user history rank" may be calculated based on frequency of past visits to a given search result by a user, which may be tracked, without limitation, in user database 136; frequency of visits by all users in cohort may be so tracked. In an embodiment, two or more of index rank, relevance rank, keyword score, user history rank, and/or inverted score may be aggregated together to calculate a numerical field, vector, or other data object determining an overall rank of a search result. Overall rank, and/or any other component score thereof, may be further weighted by and/or aggregated with, numbers representing one or more additional determinations, such as a detection of problematic content as described below.

Continuing to refer to FIG. 15, computing device is configured to output ranked search result to user. Outputting may include displaying search results in rank order, for instance in the form of a list of links to URLs from search results, each of which a user may select to navigate to web sites and/or other resources at the corresponding URL. In an embodiment, computing device may remove one or more URLs from search results, give the one or more URLs a lower ranking, and/or post a warning message next to such URLs as a result of detection of content that may be problematic to user based on user proclivities and/or behavioral history; this may be performed, without limitation, as described in U.S. Nonprovisional patent Ser. No. 16/673, 673, filed Nov. 4, 2019, and entitled "SYSTEMS AND METHODS FOR CLASSIFYING MEDIA ACCORDING TO USER NEGATIVE PROPENSITIES." Each search result list may be displayed in rank order. Computing device may look up, reconstruct, and/or mark up snippets showing context of matching keywords/phrases.

Still referring to FIG. 15, computing device and/or another device incorporated in and/or in communication with system 100 may be configured to generate physiologically linked web index, or any of indices. In an embodiment, an index may be generated by modifying ranking information in a general index as a function of a cohort; this may be performed, without limitation, by performing ranking algorithms used for general index limited to a population matching a cohort corresponding to the index to be generated. Alternatively or additionally, computing device and/or other device may produce cohort-specific index by ranking general index entries according to a cohort relevance heuristic. Cohort relevance heuristic may include, without limitation, a model that maps keywords to a relevance score, for instance using a linear combination, polynomial combination, or other mathematical expression of keyword identifications and/or frequency of appearance in a web page or other document the output of which is a relevance score. Cohort relevance heuristic may be generated using a machine-learning algorithm and using training data correlating terms with cohort member hits and/or visits to web destinations, which may be anonymously compiled by monitoring navigational choices of cohort member users.

Still referring to FIG. 15, at step 1515, at least a server receives at least a user entry containing an alimentary self-fulfillment action; this may be implemented, without limitation, as described above in reference to FIGS. 1-14.

At step 1520, and with continued reference to FIG. 15, at least a server generates a modified self-fulfillment instruction set as a function of the alimentary self-fulfillment action; this may be implemented, without limitation, as described above in reference to FIGS. 1-14. In some embodiments, generating the modified self-fulfillment instruction may include generating a modified alimentary instruction set as a function of the alimentary self-fulfillment action and generating the at least a self-fulfillment instruction set as a function of the modified alimentary instruction set. Modified alimentary instruction set may be generated, without limitation, by removing one or more alimentary elements therefrom based on user entry; for instance, and without limitation, where user entry indicates that user has consumed and/or acquired a given alimentary product, that alimentary product may be removed and/or deleted from alimentary instruction set and/or a local instance thereof.

Still referring to FIG. 15, generating at least a self-fulfillment instruction set as a function of modified alimentary instruction set may include generating the at least a self-fulfillment instruction set as a function of the modified alimentary instruction set and machine-learning model; this may be performed, without limitation, as described above in reference to FIGS. 1-14.

In an embodiment, and continuing to refer to FIG. 15, modified self-fulfillment instruction set may include generating the modified self-fulfillment instruction set as a function of the alimentary self-fulfillment action and the machine-learning model. For instance, and without limitation, machine-learning model may be trained with training data that includes training examples associating modifications with elements of self-fulfillment instruction sets, such that combinations of alimentary instruction set with alimentary self-fulfillment actions may be input to machine-learning model, which may output altered and/or modified self-fulfillment instruction sets. Alternatively or additionally, and still referring to FIG. 15, server may be configured to generate self-fulfillment instruction set by generating a loss function of user specific variables and minimizing the loss function; this may be implemented, without limitation, as described above in reference to FIGS. 1-14. User specific variable may include an ingredient standard request and/or an ingredient requirement request.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 16:
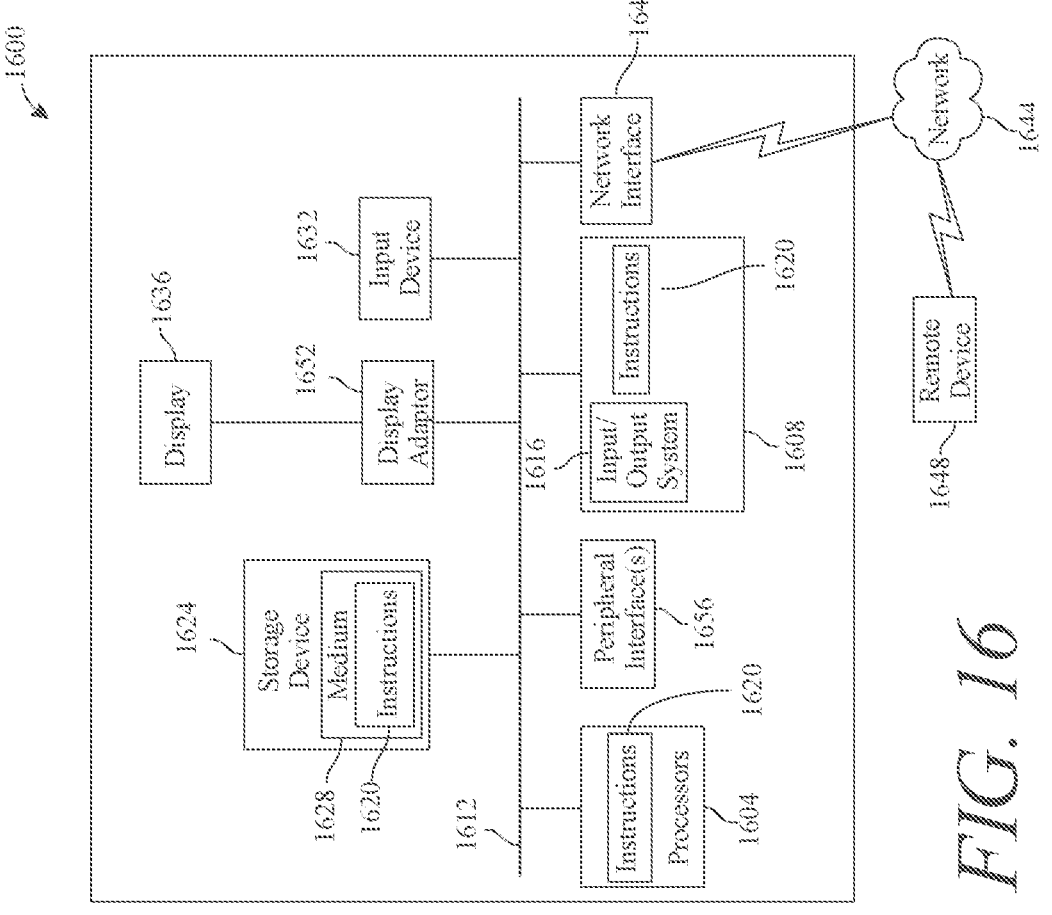
FIG. 16 is a block diagram of a computing system that can be used to implement any one or more of the methodologies disclosed herein and any one or more portions thereof.

FIG. 16 shows a diagrammatic representation of one embodiment of a computing device in the exemplary form of a computer system 1600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1600 includes a processor 1604 and a memory 1608 that communicate with each other, and with other components, via a bus 1612. Bus 1612 may include any of several types of bus structures including, but not limited to, a memory bus, a memory controller, a peripheral bus, a local bus, and any combinations thereof, using any of a variety of bus architectures.

Memory 1608 may include various components (e.g., machine-readable media) including, but not limited to, a random-access memory component, a read only component, and any combinations thereof. In one example, a basic input/output system 1616 (BIOS), including basic routines that help to transfer information between elements within computer system 1600, such as during start-up, may be stored in memory 1608. Memory 1608 may also include (e.g., stored on one or more machine-readable media) instructions (e.g., software) 1620 embodying any one or more of the aspects and/or methodologies of the present disclosure. In another example, memory 1608 may further include any number of program modules including, but not limited to, an operating system, one or more application programs, other program modules, program data, and any combinations thereof.

Computer system 1600 may also include a storage device 1624. Examples of a storage device (e.g., storage device 1624) include, but are not limited to, a hard disk drive, a magnetic disk drive, an optical disc drive in combination with an optical medium, a solid-state memory device, and any combinations thereof. Storage device 1624 may be connected to bus 1612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1624 (or one or more components thereof) may be removably interfaced with computer system 1600 (e.g., via an external port connector (not shown)). Particularly, storage device 1624 and an associated machine-readable medium 1628 may provide nonvolatile and/or volatile storage of machine-readable instructions, data structures, program modules, and/or other data for computer system 1600. In one example, software 1620 may reside, completely or partially, within machine-readable medium 1628. In another example, software 1620 may reside, completely or partially, within processor 1604.

Computer system 1600 may also include an input device 1632. In one example, a user of computer system 1600 may enter commands and/or other information into computer system 1600 via input device 1632. Examples of an input device 1632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1632 may be interfaced to bus 1612 via any of a variety of interfaces (not shown) including, but not limited to, a serial interface, a parallel interface, a game port, a USB interface, a FIRE-WIRE interface, a direct interface to bus 1612, and any combinations thereof. Input device 1632 may include a touch screen interface that may be a part of or separate from display 1636, discussed further below. Input device 1632 may be utilized as a user selection device for selecting one or more graphical representations in a graphical interface as described above.

A user may also input commands and/or other information to computer system 1600 via storage device 1624 (e.g., a removable disk drive, a flash drive, etc.) and/or network interface device 1640. A network interface device, such as network interface device 1640, may be utilized for connecting computer system 1600 to one or more of a variety of networks, such as network 1644, and one or more remote devices 1648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1644, may employ a wired and/or a wireless mode of communication. In general, any network topology may be used. Information (e.g., data, software 1620, etc.) may be communicated to and/or from computer system 1600 via network interface device 1640.

Computer system 1600 may further include a video display adapter 1652 for communicating a displayable image to a display device, such as display device 1636.

Examples of a display device include, but are not limited to, a liquid crystal display (LCD), a cathode ray tube (CRT), a plasma display, a light emitting diode (LED) display, and any combinations thereof. Display adapter 1652 and display device 1636 may be utilized in combination with processor 1604 to provide graphical representations of aspects of the present disclosure. In addition to a display device, computer system 1600 may include one or more other peripheral output devices including, but not limited to, an audio speaker, a printer, and any combinations thereof. Such peripheral output devices may be connected to bus 1612 via a peripheral interface 1656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for self-fulfillment of a dietary request, the system comprising:

at least a server, wherein the at least a server is designed and configured to:

receive an alimentary instruction set as a function of a dietary request, wherein receiving the alimentary instruction set comprises:

parsing the alimentary instruction set into a plurality of tokens;

storing the plurality of tokens as one or more chains;

assigning an alimentary label to one or more of the plurality of tokens using a Hidden Markov Model; and generating an alimentary instruction set descriptor by converting one or more alimentary labels into narrative language by retrieving one or more elements of narrative language from a table associating alimentary labels with elements of narrative language;

generate at least a self-fulfillment instruction set, the self-fulfillment instruction set comprising a data structure identifying a plurality of self-fulfilling actions a user can take to self-fulfill a suggested nourishment requirement, as a function of at least a self-fulfillment action, wherein generating the at least a self-fulfillment instruction set comprises:

receiving training data including a plurality of data entries, each data entry of the plurality of data entries including at least an alimentary instruction and at
least a correlated self-fulfillment action datum;

training a machine-learning model as a function of the
training data; and generating the at least a self-fulfillment instruction set
as a function of the alimentary instruction set and the
machine-learning model;

generating a query as a function of at least an instruc-
tion of the self-fulfillment instruction set;

querying a web index as a function of the query by
classifying, using an index classifier, the user to a
physiologically linked web index, and querying the
physiologically linked web index, wherein the index
classifier is iteratively trained with elements of
physiological data sets correlated to user cohort
labels, wherein the server is configured to continu-
ously generate, using a feature learning algorithm
implementing a clustering analysis, cohort labels,
using a feature learning algorithm, when a threshold
number of physiological data sets fails to converge
within a threshold distance of existing clusters;

receiving a search result corresponding to the query;
and modifying the at least an instruction as a function of the
search result;

receive at least an entry containing an alimentary self-
fulfillment action; and generate a modified self-fulfillment instruction set as a
function of the alimentary self-fulfillment action.

2. The system of claim 1, wherein receiving the alimen-
tary instruction set further comprises:

receiving at least a dietary request; and generating the alimentary instruction set as a function of
the at least a dietary request.

3. The system of claim 1, wherein generating the modified
self-fulfillment instruction set further comprises:

generating a modified alimentary instruction set as a
function of the alimentary self-fulfillment action; and generating the at least a self-fulfillment instruction set as
a function of the modified alimentary instruction set.

4. The system of claim 3, wherein generating the at least
a self-fulfillment instruction set as a function of the modified
alimentary instruction set further comprises generating the at
least a self-fulfillment instruction set as a function of the
modified alimentary instruction set and the machine-learn-
ing model.

5. The system of claim 1, wherein generating the modified
self-fulfillment instruction set further comprises generating
the modified self-fulfillment instruction set as a function of
the alimentary self-fulfillment action and the machine-learn-
ing model.

6. The system of claim 1, wherein the server is further
configured to generate the self-fulfillment instruction set by:

generating a loss function of user specific variables; and minimizing the loss function.

7. The system of claim 6, wherein a user specific variable
further comprises an ingredient standard request.

8. The system of claim 6, wherein a user specific variable
further comprises an ingredient requirement request.

9. A method of self-fulfillment of a dietary request, the
method comprising:

receiving, by at least a server, an alimentary instruction
set as a function of a dietary request, wherein receiving
the alimentary instruction set comprises:

parsing the alimentary instruction set into a plurality of
tokens;

storing the plurality of tokens as one or more chains;

assigning an alimentary label to one or more of the
plurality of tokens using a Hidden Markov Model;
and generating an alimentary instruction set descriptor by
converting one or more alimentary labels into nar-
rative language by retrieving one or more elements
of narrative language from a table associating ali-
mentary labels with elements of narrative language;

generating, by the at least a server, at least a self-
fulfillment instruction set, the self-fulfillment instruc-
tion set comprising a data structure identifying a plu-
rality of self-fulfilling actions a user can take to self-
fulfill a suggested nourishment requirement, as a
function of at least a self-fulfillment action, wherein
generating the at least a self-fulfillment instruction set
comprises:

receiving training data including a plurality of data
entries, each data entry of the plurality of data entries
including at least an alimentary instruction and at
least a correlated self-fulfillment action datum;

training a machine-learning model as a function of the
training data; and generating the at least a self-fulfillment instruction set
as a function of the alimentary instruction set and the
machine-learning model;

generating a query as a function of at least an instruc-
tion of the self-fulfillment instruction set;

querying a web index as a function of the query by
classifying, using an index classifier, the user to a
physiologically linked web index, and querying the
physiologically linked web index, wherein the index
classifier is iteratively trained with elements of
physiological data sets correlated to user cohort
labels, wherein the server is configured to continu-
ously generate, using a feature learning algorithm
implementing a clustering analysis, cohort labels
when a threshold number of physiological data sets
fails to converge within a threshold distance of
existing clusters;

receiving a search result corresponding to the query;
and modifying the at least an instruction as a function of the
search result;

receiving, by the at least a server, at least an entry
containing an alimentary self-fulfillment action;

generating, by the at least a server a modified self-
fulfillment instruction set as a function of the alimen-
tary self-fulfillment action.

10. The method of claim 9, wherein receiving the alimen-
tary instruction set further comprises:

receiving at least a dietary request; and generating the alimentary instruction set as a function of
the at least a dietary request.

11. The method of claim 9, wherein generating the modi-
fied self-fulfillment instruction set further comprises:

generating a modified alimentary instruction set as a
function of the alimentary self-fulfillment action; and generating the at least a self-fulfillment instruction set as
a function of the modified alimentary instruction set.

12. The method of claim 11, wherein generating the at
least a self-fulfillment instruction set as a function of the
modified alimentary instruction set further comprises gen-
erating the at least a self-fulfillment instruction set as a
function of the modified alimentary instruction set and the
machine-learning model.

13. The method of claim 9, wherein generating the
modified self-fulfillment instruction set further comprises generating the modified self-fulfillment instruction set as a function of the alimentary self-fulfillment action and the machine-learning model.

14. The method of claim 9, wherein the server is further configured to generate the self-fulfillment instruction set by:

generating a loss function of user specific variables; and minimizing the loss function.

15. The method of claim 14, wherein a user specific variable further comprises an ingredient standard request.

16. The method of claim 14, wherein a user specific variable further comprises an ingredient requirement request.

17. The system of claim 1, wherein generating the cohort labels using the feature learning algorithm comprises:

dividing physiological data from a given user into a plurality of sub-combinations to create a plurality of physiological data sets using a cluster analysis; and evaluating which physiological data sets tend to co-occur with which other physiological data sets as a function of a degree of similarity index value, wherein the cluster analysis is configured to configured to:

generate an initial set of user cohort labels from an initial set of user physiological data; and iteratively identify new clusters to generate new user cohort labels.

18. The method of claim 9, wherein generating the cohort labels using the feature learning algorithm comprises:

dividing physiological data from a given user into a plurality of sub-combinations to create a plurality of physiological data sets using a cluster analysis; and evaluating which physiological data sets tend to co-occur with which other physiological data sets as a function of a degree of similarity index value, wherein the cluster analysis is configured to configured to:

generate an initial set of user cohort labels from an initial set of user physiological data; and iteratively identify new clusters to generate new user cohort labels.

* * * * *